US007613491B2

(12) United States Patent
Boock et al.

(10) Patent No.: US 7,613,491 B2
(45) Date of Patent: Nov. 3, 2009

(54) SILICONE BASED MEMBRANES FOR USE IN IMPLANTABLE GLUCOSE SENSORS

(75) Inventors: Robert Boock, San Diego, CA (US); Monica Rixman, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 474 days.

(21) Appl. No.: 11/404,417

(22) Filed: Apr. 14, 2006

(65) Prior Publication Data

US 2007/0244379 A1 Oct. 18, 2007

(51) Int. Cl.
*A61B 5/00* (2006.01)
*C08J 9/00* (2006.01)

(52) U.S. Cl. .......................... 600/347; 600/365; 521/50

(58) Field of Classification Search ....................... None
See application file for complete search history.

(56) References Cited

U.S. PATENT DOCUMENTS 3,220,960 A 11/1965 Lim et al.
3,562,352 A 2/1971 Nyilas
3,746,588 A 7/1973 Brown, Jr.
3,837,339 A 9/1974 Aisenberg
3,874,850 A 4/1975 Sorensen et al.
3,926,760 A 12/1975 Allen et al.
3,966,580 A 6/1976 Janata et al.
3,979,274 A 9/1976 Newman
4,008,717 A 2/1977 Kowarski
4,016,866 A 4/1977 Lawton
4,024,312 A 5/1977 Korpman
4,040,908 A 8/1977 Clark, Jr.
4,073,713 A 2/1978 Newman
4,076,656 A 2/1978 White et al.
4,136,250 A 1/1979 Mueller et al.
4,197,840 A 4/1980 Beck et al.
4,240,889 A 12/1980 Yoda et al.
4,256,561 A 3/1981 Schindler et al.
4,260,725 A 4/1981 Keogh et al.
4,292,423 A 9/1981 Kaufmann et al.
4,327,725 A 5/1982 Cortese et al.
4,388,166 A 6/1983 Suzuki et al.
4,415,666 A 11/1983 D'Orazio et al.
4,418,148 A 11/1983 Oberhardt
4,431,507 A 2/1984 Nankai et al.
4,453,537 A 6/1984 Spitzer
4,484,987 A 11/1984 Gough
4,486,290 A 12/1984 Cahalan et al.
4,492,575 A 1/1985 Mabille
4,493,714 A 1/1985 Ueda et al.
4,506,680 A 3/1985 Stokes
4,519,973 A 5/1985 Cahalan et al.

(Continued)

FOREIGN PATENT DOCUMENTS

EP 0 107 634 5/1984

(Continued)

OTHER PUBLICATIONS

Notification of Transmittal of the International Search Report and the Written Opinion of the International Searching Authority, or the Declaration, dated Jul. 5, 2007.

(Continued)

*Primary Examiner*—Robert L Nasser
(74) *Attorney, Agent, or Firm*—Knobbe Martens Olson & Bear LLP

(57) ABSTRACT

Membrane systems incorporating silicone polymers are described for use in implantable analyte sensors. Some layers of the membrane system may comprise a blend of a silicone polymer with a hydrophilic polymer, for example, a triblock poly(ethylene oxide)-poly(propylene oxide)-poly(ethylene oxide) polymer. Such polymeric blends provide for both high oxygen solubility and aqueous analyte solubility.

59 Claims, 8 Drawing Sheets

8
18
10
14
16

U.S. PATENT DOCUMENTS 4,527,999 A 7/1985 Lee
4,534,355 A 8/1985 Potter
4,538,616 A 9/1985 Rogoff
4,545,382 A 10/1985 Higgins et al.
4,565,665 A 1/1986 Fogt
4,565,666 A 1/1986 Cahalan et al.
4,568,444 A 2/1986 Nakamura et al.
4,577,642 A 3/1986 Stokes
4,592,824 A 6/1986 Smith et al.
4,600,495 A 7/1986 Fogt
4,602,922 A 7/1986 Cabasso et al.
4,632,968 A 12/1986 Yokota et al.
4,644,046 A 2/1987 Yamada
4,647,643 A 3/1987 Zdrabala et al.
4,650,547 A 3/1987 Gough
4,663,824 A 5/1987 Kenmochi
4,671,288 A 6/1987 Gough
4,675,346 A 6/1987 Lin et al.
4,680,268 A 7/1987 Clark, Jr.
4,684,538 A 8/1987 Klemarczyk
4,685,463 A 8/1987 Williams
4,686,137 A 8/1987 Ward, Jr. et al.
4,689,149 A 8/1987 Kanno et al.
4,689,309 A 8/1987 Jones
4,694,861 A 9/1987 Goodale et al.
4,702,732 A 10/1987 Powers et al.
4,703,756 A 11/1987 Gough et al.
4,711,245 A 12/1987 Higgins et al.
4,711,251 A 12/1987 Stokes
4,721,677 A 1/1988 Clark, Jr.
4,726,381 A 2/1988 Jones
4,753,652 A 6/1988 Langer et al.
4,757,022 A 7/1988 Shults et al.
4,759,828 A 7/1988 Young et al.
4,763,658 A 8/1988 Jones
4,776,944 A 10/1988 Janata et al.
4,777,953 A 10/1988 Ash et al.
4,781,733 A 11/1988 Babcock et al.
4,786,657 A 11/1988 Hammar et al.
4,793,555 A 12/1988 Lee et al.
4,795,542 A 1/1989 Ross et al.
4,803,243 A 2/1989 Fujimoto et al.
4,809,704 A 3/1989 Sogawa et al.
4,810,470 A 3/1989 Burkhardt et al.
4,820,281 A 4/1989 Lawler
4,822,336 A 4/1989 DiTraglia
4,828,544 A 5/1989 Lane et al.
4,834,101 A 5/1989 Collison et al.
4,841,974 A 6/1989 Gumbriecht et al.
4,849,458 A 7/1989 Reed et al.
4,854,322 A 8/1989 Ash et al.
4,861,830 A 8/1989 Ward, Jr.
4,867,741 A 9/1989 Portnoy
4,880,883 A 11/1989 Grasel et al.
4,886,740 A 12/1989 Vadgama
4,889,744 A 12/1989 Quaid
4,890,620 A 1/1990 Gough
4,902,294 A 2/1990 Gosserez
4,907,857 A 3/1990 Giuliani et al.
4,908,208 A 3/1990 Lee et al.
4,909,908 A 3/1990 Ross et al.
4,919,141 A 4/1990 Zier et al.
4,934,375 A 6/1990 Cole et al.
4,935,345 A 6/1990 Guilbeau et al.
4,951,657 A 8/1990 Pfister et al.
4,963,595 A 10/1990 Ward et al.
4,967,940 A 11/1990 Blette et al.
4,970,145 A 11/1990 Bennetto et al.
4,973,320 A 11/1990 Brenner et al.
4,974,929 A 12/1990 Curry
4,979,509 A 12/1990 Hakky
4,986,671 A 1/1991 Sun et al.
4,994,026 A 2/1991 Fecondini
4,994,167 A 2/1991 Shults et al.
5,002,572 A 3/1991 Picha
5,002,590 A 3/1991 Friesen et al.
5,006,050 A 4/1991 Cooke et al.
5,006,111 A 4/1991 Inokuchi et al.
5,007,929 A 4/1991 Quaid
5,009,251 A 4/1991 Pike et al.
5,030,199 A 7/1991 Barwick et al.
5,034,461 A 7/1991 Lai et al.
5,035,711 A 7/1991 Aoki et al.
5,041,092 A 8/1991 Barwick
5,055,198 A 10/1991 Shettigar
5,063,081 A 11/1991 Cozzette et al.
5,067,491 A 11/1991 Taylor, II et al.
5,070,169 A 12/1991 Robertson et al.
5,071,452 A 12/1991 Avrillon et al.
5,109,850 A 5/1992 Blanco et al.
5,112,301 A 5/1992 Fenton et al.
5,113,871 A 5/1992 Viljanto et al.
5,120,813 A 6/1992 Ward, Jr.
5,128,408 A 7/1992 Tanaka et al.
5,147,725 A 9/1992 Pinchuk
5,155,149 A 10/1992 Atwater et al.
5,165,407 A 11/1992 Wilson et al.
5,169,906 A 12/1992 Cray et al.
5,174,291 A 12/1992 Schoonen et al.
5,182,004 A 1/1993 Kohno
5,183,549 A 2/1993 Joseph et al.
5,200,051 A 4/1993 Cozzette et al.
5,202,261 A 4/1993 Musho et al.
5,208,313 A 5/1993 Krishnan
5,212,050 A 5/1993 Mier et al.
5,220,917 A 6/1993 Cammilli et al.
5,221,724 A 6/1993 Li et al.
5,235,003 A 8/1993 Ward et al.
5,242,835 A 9/1993 Jensen
5,249,576 A 10/1993 Goldberger et al.
5,250,439 A 10/1993 Musho et al.
5,271,736 A 12/1993 Picha
5,282,848 A 2/1994 Schmitt
5,284,140 A 2/1994 Allen et al.
5,286,364 A 2/1994 Yacynych et al.
5,296,144 A 3/1994 Sternina et al.
5,299,571 A 4/1994 Mastrototaro
5,314,471 A 5/1994 Brauker et al.
5,316,452 A 5/1994 Bogen et al.
5,322,063 A 6/1994 Allen et al.
5,326,356 A 7/1994 Della Valle et al.
5,326,449 A 7/1994 Cunningham
5,330,521 A 7/1994 Cohen
5,330,634 A 7/1994 Wong et al.
5,337,747 A 8/1994 Neftel
5,340,352 A 8/1994 Nakanishi et al.
5,342,693 A 8/1994 Winters et al.
5,342,789 A 8/1994 Chick et al.
5,344,451 A 9/1994 Dayton
5,344,454 A 9/1994 Clarke et al.
5,348,788 A 9/1994 White
5,352,348 A 10/1994 Young et al.
5,372,133 A 12/1994 Hogen Esch
5,380,665 A 1/1995 Cusack et al.
5,387,327 A 2/1995 Khan
5,397,848 A 3/1995 Yang et al.
5,411,052 A 5/1995 Murray
5,423,738 A 6/1995 Robinson et al.
5,426,158 A 6/1995 Mueller et al.
5,428,123 A 6/1995 Ward et al.
5,431,921 A 7/1995 Thombre
5,443,508 A 8/1995 Giampapa
5,453,278 A 9/1995 Chan et al.
5,458,631 A 10/1995 Xavier et al.

5,462,064 A 10/1995 D'Angelo et al.
5,466,575 A 11/1995 Cozzette et al.
5,469,846 A 11/1995 Khan
5,476,094 A 12/1995 Allen et al.
5,482,446 A 1/1996 Williamson et al.
5,482,473 A 1/1996 Lord et al.
5,484,404 A 1/1996 Schulman et al.
5,494,562 A 2/1996 Maley et al.
5,497,772 A 3/1996 Schulman et al.
5,505,828 A 4/1996 Wong et al.
5,509,888 A 4/1996 Miller
5,512,055 A 4/1996 Domb et al.
5,514,253 A 5/1996 Davis et al.
5,520,788 A 5/1996 Johnson
5,521,273 A 5/1996 Yilgor et al.
5,531,679 A 7/1996 Schulman et al.
5,538,511 A 7/1996 Van Antwerp
5,541,305 A 7/1996 Yokota et al.
5,545,220 A 8/1996 Andrews et al.
5,545,223 A 8/1996 Neuenfeldt et al.
5,549,651 A 8/1996 Lynn
5,549,675 A 8/1996 Neuenfeldt et al.
5,551,850 A 9/1996 Williamson et al.
5,552,112 A 9/1996 Schiffmann
5,554,339 A 9/1996 Cozzette
5,564,439 A 10/1996 Picha
5,569,219 A 10/1996 Hakki et al.
5,575,930 A 11/1996 Tietje-Girault et al.
5,584,876 A 12/1996 Bruchman et al.
5,586,553 A 12/1996 Halili et al.
5,587,273 A 12/1996 Yan et al.
5,589,563 A 12/1996 Ward et al.
5,593,440 A 1/1997 Brauker et al.
5,593,852 A 1/1997 Heller et al.
5,605,152 A 2/1997 Slate et al.
5,611,900 A 3/1997 Worden
5,624,537 A 4/1997 Turner et al.
5,626,563 A 5/1997 Dodge et al.
5,628,619 A 5/1997 Wilson
5,628,890 A 5/1997 Carter et al.
5,630,978 A 5/1997 Domb
5,637,083 A 6/1997 Bertrand et al.
5,637,135 A 6/1997 Ottenstein et al.
5,640,470 A 6/1997 Iyer et al.
5,651,767 A 7/1997 Schulman et al.
5,653,756 A 8/1997 Clarke et al.
5,658,330 A 8/1997 Carlisle et al.
5,660,163 A 8/1997 Schulman et al.
5,665,222 A 9/1997 Heller et al.
5,673,694 A 10/1997 Rivers
5,676,651 A 10/1997 Larson et al.
5,681,572 A 10/1997 Seare
5,683,562 A 11/1997 Schaffar et al.
5,688,239 A 11/1997 Walker
5,703,359 A 12/1997 Wampler, III
5,704,354 A 1/1998 Priedel et al.
5,706,807 A 1/1998 Picha
5,711,861 A 1/1998 Ward et al.
5,713,888 A 2/1998 Neuenfeldt et al.
5,733,336 A 3/1998 Neuenfeldt et al.
5,741,330 A 4/1998 Brauker et al.
5,746,898 A 5/1998 Priedel
5,756,632 A 5/1998 Ward et al.
5,760,155 A 6/1998 Mowrer et al.
5,773,270 A 6/1998 D'Orazio et al.
5,773,286 A 6/1998 Dionne et al.
5,777,060 A 7/1998 Van Antwerp
5,782,912 A 7/1998 Brauker et al.
5,783,054 A 7/1998 Raguse et al.
5,787,900 A 8/1998 Butler et al.
5,791,344 A 8/1998 Schulman et al.
5,791,880 A 8/1998 Wilson
5,795,453 A 8/1998 Gilmartin
5,795,774 A 8/1998 Matsumoto et al.
5,798,065 A 8/1998 Picha
5,800,420 A 9/1998 Gross et al.
5,800,529 A 9/1998 Brauker et al.
5,804,048 A 9/1998 Wong et al.
5,807,406 A 9/1998 Brauker et al.
5,811,487 A 9/1998 Schulz, Jr. et al.
5,820,589 A 10/1998 Torgerson et al.
5,833,603 A 11/1998 Kovacs et al.
5,836,887 A 11/1998 Oka et al.
5,837,454 A 11/1998 Cozzette et al.
5,840,026 A 11/1998 Uber et al.
5,858,296 A 1/1999 Domb
5,863,972 A 1/1999 Beckelmann et al.
5,871,514 A 2/1999 Wiklund et al.
5,873,862 A 2/1999 Lopez
5,879,713 A 3/1999 Roth et al.
5,882,354 A 3/1999 Brauker et al.
5,882,494 A 3/1999 Van Antwerp
5,897,578 A 4/1999 Wiklund et al.
5,913,998 A 6/1999 Butler et al.
5,914,026 A 6/1999 Blubaugh, Jr. et al.
5,917,346 A 6/1999 Gord
5,919,215 A 7/1999 Wiklund et al.
5,928,155 A 7/1999 Eggers et al.
5,928,182 A 7/1999 Kraus et al.
5,928,195 A 7/1999 Malamud et al.
5,932,175 A 8/1999 Knute et al.
5,935,785 A 8/1999 Reber et al.
5,957,854 A 9/1999 Besson et al.
5,964,261 A 10/1999 Neuenfeldt et al.
5,964,745 A 10/1999 Lyles et al.
5,964,804 A 10/1999 Brauker et al.
5,964,993 A 10/1999 Blubaugh et al.
5,965,380 A 10/1999 Heller et al.
5,972,199 A 10/1999 Heller
5,985,129 A 11/1999 Gough et al.
5,987,352 A 11/1999 Klein et al.
5,999,848 A 12/1999 Gord et al.
6,001,067 A 12/1999 Shults et al.
6,001,471 A 12/1999 Bries et al.
6,002,954 A 12/1999 Van Antwerp et al.
6,011,984 A 1/2000 Van Antwerp et al.
6,014,577 A 1/2000 Henning et al.
6,015,572 A 1/2000 Lin et al.
6,017,435 A 1/2000 Hassard et al.
6,018,033 A * 1/2000 Chen et al. .................. 536/4.1
6,030,827 A 2/2000 Davis et al.
6,032,059 A 2/2000 Henning et al.
6,043,328 A 3/2000 Domschke et al.
6,045,671 A 4/2000 Wu et al.
6,048,691 A 4/2000 Maracas
6,051,372 A 4/2000 Bayerl et al.
6,055,456 A 4/2000 Gerber
6,057,377 A 5/2000 Sasaki et al.
6,063,637 A 5/2000 Arnold et al.
6,066,448 A 5/2000 Wohlstadter et al.
6,077,299 A 6/2000 Adelberg et al.
6,081,736 A 6/2000 Colvin et al.
6,083,523 A 7/2000 Dionne et al.
6,083,710 A 7/2000 Heller et al.
6,088,608 A 7/2000 Schulman et al.
6,103,033 A 8/2000 Say et al.
6,103,533 A 8/2000 Hassard et al.
6,119,028 A 9/2000 Schulman et al.
6,121,009 A 9/2000 Heller et al.
6,123,827 A 9/2000 Wong et al.
6,127,154 A 10/2000 Mosbach et al.
6,134,461 A 10/2000 Say et al.
6,157,860 A 12/2000 Hauser et al.
6,162,611 A 12/2000 Heller et al.
6,164,921 A 12/2000 Moubayed et al.
6,175,752 B1 1/2001 Say et al.

6,183,437 B1 2/2001 Walker
6,189,536 B1 2/2001 Martinez et al.
6,201,980 B1 3/2001 Darrow et al.
6,212,416 B1 4/2001 Ward et al.
6,213,739 B1 4/2001 Phallen et al.
6,214,185 B1 4/2001 Offenbacher et al.
6,223,080 B1 4/2001 Thompson
6,231,879 B1 5/2001 Li et al.
6,248,067 B1 6/2001 Causey, III et al.
6,251,280 B1 6/2001 Dai et al.
6,254,586 B1 7/2001 Mann et al.
6,256,522 B1 7/2001 Schultz
6,259,937 B1 7/2001 Schulman et al.
6,264,825 B1 7/2001 Blackburn et al.
6,271,332 B1 8/2001 Lohmann et al.
6,272,382 B1 8/2001 Faltys et al.
6,274,285 B1 8/2001 Gries et al.
6,281,015 B1 8/2001 Mooney et al.
6,284,478 B1 9/2001 Heller et al.
6,293,925 B1 9/2001 Safabash et al.
6,299,583 B1 10/2001 Eggers et al.
6,306,594 B1 10/2001 Cozzette
6,309,384 B1 10/2001 Harrington et al.
6,310,110 B1 10/2001 Markowitz et al.
6,312,706 B1 11/2001 Lai et al.
6,315,738 B1 11/2001 Nishikawa et al.
6,319,566 B1 11/2001 Polanyi et al.
6,325,978 B1 12/2001 Labuda et al.
6,325,979 B1 12/2001 Hahn et al.
6,329,161 B1 12/2001 Heller et al.
6,330,464 B1 12/2001 Colvin, Jr. et al.
6,343,225 B1 1/2002 Clark, Jr.
6,365,670 B1 4/2002 Fry
6,372,244 B1 4/2002 Antanavich et al.
6,379,883 B2 4/2002 Davis et al.
6,391,019 B1 5/2002 Ito
6,405,066 B1 6/2002 Essenpreis et al.
6,407,195 B2 6/2002 Sherman et al.
6,413,393 B1 7/2002 Van Antwerp et al.
6,442,413 B1 8/2002 Silver
6,447,448 B1 9/2002 Ishikawa et al.
6,447,542 B1 9/2002 Weadock
6,454,710 B1 9/2002 Ballerstadt et al.
6,459,917 B1 10/2002 Gowda et al.
6,461,496 B1 10/2002 Feldman et al.
6,465,066 B1 10/2002 Rule et al.
6,466,810 B1 10/2002 Ward et al.
6,467,480 B1 10/2002 Meier et al.
6,471,689 B1 10/2002 Joseph et al.
6,477,392 B1 11/2002 Honigs et al.
6,477,395 B2 11/2002 Schulman et al.
6,484,045 B1 11/2002 Holker et al.
6,484,046 B1 11/2002 Say et al.
6,485,449 B2 11/2002 Ito
6,488,652 B1 12/2002 Weijand et al.
6,494,879 B2 12/2002 Lennox et al.
6,497,729 B1 12/2002 Moussy et al.
6,498,043 B1 12/2002 Schulman et al.
6,498,941 B1 12/2002 Jackson
6,512,939 B1 1/2003 Colvin et al.
6,514,718 B2 2/2003 Heller et al.
6,520,326 B2 2/2003 McIvor et al.
6,520,477 B2 2/2003 Trimmer
6,520,937 B2 2/2003 Hart et al.
6,520,997 B1 2/2003 Pekkarinen et al.
6,526,298 B1 2/2003 Khalil et al.
6,528,584 B2 3/2003 Kennedy et al.
6,537,318 B1 3/2003 Ita et al.
6,541,107 B1 4/2003 Zhong et al.
6,542,765 B1 4/2003 Guy et al.
6,545,085 B2 4/2003 Kilgour et al.
6,546,268 B1 4/2003 Ishikawa et al.
6,547,839 B2 4/2003 Zhang et al.
6,551,496 B1 4/2003 Moles et al.
6,553,244 B2 4/2003 Lesho et al.
6,554,822 B1 4/2003 Holschneider et al.
6,558,321 B1 5/2003 Burd et al.
6,560,471 B1 5/2003 Heller et al.
6,565,509 B1 5/2003 Say et al.
6,565,807 B1 5/2003 Patterson et al.
6,569,521 B1 5/2003 Sheridan et al.
6,574,490 B2 6/2003 Abbink et al.
6,576,461 B2 6/2003 Heller et al.
6,579,498 B1 6/2003 Eglise
6,579,690 B1 6/2003 Bonnecaze et al.
6,585,763 B1 7/2003 Keilman et al.
6,595,756 B2 7/2003 Gray et al.
6,602,221 B1 8/2003 Saravia et al.
6,607,509 B2 8/2003 Bobroff et al.
6,613,379 B2 9/2003 Ward et al.
6,618,934 B1 9/2003 Feldman et al.
6,633,772 B2 10/2003 Ford et al.
6,642,015 B2 11/2003 Vachon et al.
6,654,625 B1 11/2003 Say et al.
6,656,157 B1 12/2003 Duchon et al.
6,663,615 B1 12/2003 Madou et al.
6,670,115 B1 12/2003 Zhang
6,673,596 B1 1/2004 Sayler et al.
6,689,265 B2 2/2004 Heller et al.
6,699,218 B2 3/2004 Flaherty et al.
6,702,857 B2 3/2004 Brauker et al.
6,705,833 B2 3/2004 Tam et al.
6,721,587 B2 4/2004 Gough
6,741,877 B1 5/2004 Shults et al.
6,749,587 B2 6/2004 Flaherty
6,770,030 B1 8/2004 Schaupp et al.
6,770,067 B2 8/2004 Lorenzen et al.
6,780,297 B2 8/2004 Matsumoto et al.
6,784,274 B2 8/2004 van Antwerp et al.
6,793,632 B2 9/2004 Sohrab
6,801,041 B2 10/2004 Karinka et al.
6,805,693 B2 10/2004 Gray et al.
6,809,507 B2 10/2004 Morgan et al.
6,809,653 B1 10/2004 Mann et al.
6,814,845 B2 11/2004 Wilson et al.
6,815,186 B2 11/2004 Clark, Jr.
6,862,465 B2 3/2005 Shults et al.
6,875,386 B1 4/2005 Ward et al.
6,881,551 B2 4/2005 Heller et al.
6,891,317 B2 5/2005 Pei et al.
6,892,085 B2 5/2005 McIvor et al.
6,893,552 B1 5/2005 Wang et al.
6,895,265 B2 5/2005 Silver
6,913,626 B2 7/2005 McGhan et al.
6,926,691 B2 8/2005 Miethke
6,932,584 B2 8/2005 Gray et al.
6,932,894 B2 8/2005 Mao et al.
6,936,006 B2 8/2005 Sabra
6,960,192 B1 11/2005 Flaherty et al.
6,966,325 B2 11/2005 Erickson
6,973,706 B2 12/2005 Say et al.
6,975,893 B2 12/2005 Say et al.
6,989,891 B2 1/2006 Braig et al.
6,997,921 B2 2/2006 Gray et al.
7,008,979 B2 3/2006 Schottman et al.
7,025,727 B2 4/2006 Brockway et al.
7,033,322 B2 4/2006 Silver
7,061,593 B2 6/2006 Braig et al.
7,066,884 B2 6/2006 Custer et al.
7,070,577 B1 7/2006 Haller et al.
7,097,775 B2 8/2006 Greenberg et al.
7,098,803 B2 8/2006 Mann et al.
7,110,803 B2 9/2006 Shults et al.
7,120,483 B2 10/2006 Russell et al.
7,131,967 B2 11/2006 Gray et al.
7,134,999 B2 11/2006 Brauker et al.

7,136,689 B2 11/2006 Shults et al.
7,150,741 B2 12/2006 Erickson et al.
7,192,450 B2 3/2007 Brauker et al.
7,241,586 B2 7/2007 Gulati
7,247,138 B2 7/2007 Reghabi et al.
7,248,906 B2 7/2007 Dirac et al.
7,254,450 B2 8/2007 Christopherson et al.
7,255,690 B2 8/2007 Gray et al.
7,279,174 B2 10/2007 Pacetti et al.
7,288,085 B2 10/2007 Olsen
7,316,662 B2 1/2008 Delnevo et al.
7,318,814 B2 1/2008 Levine et al.
7,329,234 B2 2/2008 Sansoucy
7,335,195 B2 2/2008 Mehier
7,335,286 B2 2/2008 Abel et al.
7,336,984 B2 2/2008 Gough et al.
7,357,793 B2 4/2008 Pacetti
7,361,155 B2 4/2008 Sage et al.
7,364,562 B2 4/2008 Braig et al.
7,366,566 B2 4/2008 Henry et al.
7,379,765 B2 5/2008 Petisce et al.
7,396,353 B2 7/2008 Lorenzen et al.
2002/0009810 A1 1/2002 O'Connor et al.
2002/0018843 A1 2/2002 Van Antwerp et al.
2002/0019330 A1 2/2002 Murray et al.
2002/0023852 A1 2/2002 McIvor et al.
2002/0042561 A1 4/2002 Schulman et al.
2002/0065453 A1 5/2002 Lesho et al.
2002/0068860 A1 6/2002 Clark, Jr.
2002/0119711 A1 8/2002 Van Antwerp et al.
2002/0123087 A1 9/2002 Vachon et al.
2002/0133224 A1 9/2002 Bajgar et al.
2002/0137193 A1 9/2002 Heller et al.
2002/0151796 A1 10/2002 Koulik
2002/0182241 A1 12/2002 Boerenstein et al.
2002/0188185 A1 12/2002 Sohrab
2003/0004457 A1 1/2003 Andersson
2003/0006669 A1 1/2003 Pei et al.
2003/0009093 A1 1/2003 Silver
2003/0031699 A1 2/2003 Van Antwerp
2003/0032874 A1 2/2003 Rhodes et al.
2003/0036803 A1 2/2003 McGhan et al.
2003/0059631 A1 3/2003 Al-Lamee
2003/0065254 A1 4/2003 Schulman et al.
2003/0069383 A1 4/2003 Van Antwerp et al.
2003/0072741 A1 4/2003 Berglund et al.
2003/0076082 A1 4/2003 Morgan et al.
2003/0078481 A1 4/2003 McIvor et al.
2003/0078560 A1 4/2003 Miller et al.
2003/0088166 A1 5/2003 Say et al.
2003/0091433 A1 5/2003 Tam et al.
2003/0099682 A1 5/2003 Moussy et al.
2003/0100040 A1 5/2003 Bonnecaze et al.
2003/0104119 A1 6/2003 Wilson et al.
2003/0125613 A1 7/2003 Enegren et al.
2003/0132227 A1 7/2003 Geisler
2003/0134347 A1 7/2003 Heller et al.
2003/0188427 A1 10/2003 Say et al.
2003/0199744 A1 10/2003 Buse et al.
2003/0199745 A1 10/2003 Burson et al.
2003/0211050 A1 11/2003 Majeti et al.
2003/0217966 A1 11/2003 Tapsak et al.
2003/0225324 A1 12/2003 Anderson et al.
2003/0228681 A1 12/2003 Ritts et al.
2004/0006263 A1 1/2004 Anderson et al.
2004/0010207 A1 1/2004 Flaherty et al.
2004/0023253 A1 2/2004 Kunwar et al.
2004/0023317 A1 2/2004 Motamedi et al.
2004/0030294 A1 2/2004 Mahurkar
2004/0039406 A1 2/2004 Jessen
2004/0045879 A1 3/2004 Shults et al.
2004/0054352 A1 3/2004 Adams et al.
2004/0063167 A1 4/2004 Kaastrup et al.
2004/0074785 A1 4/2004 Holker
2004/0078219 A1 4/2004 Kaylor
2004/0106857 A1 6/2004 Gough
2004/0111017 A1 6/2004 Say et al.
2004/0138543 A1 7/2004 Russell et al.
2004/0146909 A1 7/2004 Duong et al.
2004/0152187 A1 8/2004 Haight et al.
2004/0167801 A1 8/2004 Say et al.
2004/0176672 A1 9/2004 Silver et al.
2004/0180391 A1 9/2004 Gratzl et al.
2004/0186362 A1 9/2004 Brauker et al.
2004/0219664 A1 11/2004 Heller et al.
2004/0224001 A1 11/2004 Pacetti et al.
2004/0234575 A1 11/2004 Horres et al.
2004/0248282 A1 12/2004 Sobha et al.
2004/0253365 A1 12/2004 Warren et al.
2004/0254433 A1 12/2004 Bandis
2005/0003399 A1 1/2005 Blackburn et al.
2005/0026689 A1 2/2005 Marks
2005/0031689 A1 2/2005 Shults et al.
2005/0033132 A1 2/2005 Shults et al.
2005/0051427 A1 3/2005 Brauker et al.
2005/0051440 A1 3/2005 Simpson et al.
2005/0056552 A1 3/2005 Simpson et al.
2005/0070770 A1 3/2005 Dirac et al.
2005/0077584 A1 4/2005 Uhland et al.
2005/0079200 A1 4/2005 Rathenow et al.
2005/0090607 A1 4/2005 Tapsak et al.
2005/0103625 A1 5/2005 Rhodes et al.
2005/0107677 A1 5/2005 Ward et al.
2005/0115832 A1 6/2005 Simpson et al.
2005/0118344 A1 6/2005 Pacetti
2005/0119720 A1 6/2005 Gale et al.
2005/0121322 A1 6/2005 Say
2005/0143635 A1 6/2005 Kamath et al.
2005/0154271 A1 7/2005 Rasdal et al.
2005/0154272 A1 7/2005 Dirac et al.
2005/0161346 A1 7/2005 Simpson et al.
2005/0176136 A1 8/2005 Burd et al.
2005/0176678 A1 8/2005 Horres et al.
2005/0177036 A1 8/2005 Shults et al.
2005/0181012 A1 8/2005 Saint et al.
2005/0182451 A1 8/2005 Griffin et al.
2005/0192557 A1 9/2005 Brauker et al.
2005/0197554 A1 9/2005 Polcha
2005/0203360 A1 9/2005 Brauker et al.
2005/0242479 A1 11/2005 Petisce et al.
2005/0245795 A1 11/2005 Goode et al.
2005/0245799 A1 11/2005 Brauker et al.
2005/0251083 A1 11/2005 Carr-Brendel et al.
2005/0282997 A1 12/2005 Ward
2005/0288596 A1 12/2005 Eigler et al.
2006/0001550 A1 1/2006 Mann et al.
2006/0003398 A1 1/2006 Heller et al.
2006/0015020 A1 1/2006 Neale et al.
2006/0015024 A1 1/2006 Brister et al.
2006/0016700 A1 1/2006 Brister et al.
2006/0019327 A1 1/2006 Brister et al.
2006/0020186 A1 1/2006 Brister et al.
2006/0020187 A1 1/2006 Brister et al.
2006/0020188 A1 1/2006 Kamath et al.
2006/0020189 A1 1/2006 Brister et al.
2006/0020190 A1 1/2006 Kamath et al.
2006/0020191 A1 1/2006 Brister et al.
2006/0020192 A1 1/2006 Brister et al.
2006/0036139 A1 2/2006 Brister et al.
2006/0036140 A1 2/2006 Brister et al.
2006/0036141 A1 2/2006 Kamath et al.
2006/0036142 A1 2/2006 Brister et al.
2006/0036143 A1 2/2006 Brister et al.
2006/0036144 A1 2/2006 Brister et al.
2006/0036145 A1 2/2006 Brister et al.
2006/0047095 A1 3/2006 Pacetti

| | | | |
|---|---|---|---|
| 2006/0052745 | A1 | 3/2006 | Van Antwerp et al. |
| 2006/0067908 | A1 | 3/2006 | Ding |
| 2006/0078908 | A1 | 4/2006 | Pitner et al. |
| 2006/0079740 | A1 | 4/2006 | Silver et al. |
| 2006/0079809 | A1 | 4/2006 | Goldberger et al. |
| 2006/0094946 | A1 | 5/2006 | Kellogg et al. |
| 2006/0134165 | A1 | 6/2006 | Pacetti |
| 2006/0142651 | A1 | 6/2006 | Brister et al. |
| 2006/0155180 | A1 | 7/2006 | Brister et al. |
| 2006/0159981 | A1 | 7/2006 | Heller |
| 2006/0171980 | A1 | 8/2006 | Helmus et al. |
| 2006/0177379 | A1 | 8/2006 | Asgari |
| 2006/0183178 | A1 | 8/2006 | Gulati |
| 2006/0183871 | A1 | 8/2006 | Ward et al. |
| 2006/0189856 | A1 | 8/2006 | Petisce et al. |
| 2006/0189863 | A1 | 8/2006 | Peyser et al. |
| 2006/0195029 | A1 | 8/2006 | Shults et al. |
| 2006/0198864 | A1 | 9/2006 | Shults et al. |
| 2006/0200019 | A1 | 9/2006 | Petisce et al. |
| 2006/0200970 | A1 | 9/2006 | Brister et al. |
| 2006/0204536 | A1 | 9/2006 | Shults et al. |
| 2006/0229512 | A1 | 10/2006 | Petisce et al. |
| 2006/0253085 | A1 | 11/2006 | Geismar et al. |
| 2006/0258761 | A1 | 11/2006 | Boock et al. |
| 2006/0263673 | A1* | 11/2006 | Kim et al. .................... 429/40 |
| 2006/0263839 | A1 | 11/2006 | Ward et al. |
| 2006/0269586 | A1 | 11/2006 | Pacetti |
| 2006/0275857 | A1 | 12/2006 | Kjaer et al. |
| 2006/0275859 | A1 | 12/2006 | Kjaer |
| 2006/0289307 | A1 | 12/2006 | Yu et al. |
| 2006/0293487 | A1 | 12/2006 | Gaymans et al. |
| 2007/0007133 | A1 | 1/2007 | Mang et al. |
| 2007/0032717 | A1 | 2/2007 | Brister et al. |
| 2007/0032718 | A1 | 2/2007 | Shults et al. |
| 2007/0038044 | A1 | 2/2007 | Dobbles et al. |
| 2007/0129524 | A1 | 6/2007 | Sunkara |
| 2007/0135698 | A1 | 6/2007 | Shah et al. |
| 2007/0163880 | A1 | 7/2007 | Woo et al. |
| 2007/0173709 | A1 | 7/2007 | Petisce et al. |
| 2007/0173710 | A1 | 7/2007 | Petisce et al. |
| 2007/0197890 | A1 | 8/2007 | Boock et al. |
| 2007/0200267 | A1 | 8/2007 | Tsai |
| 2007/0213611 | A1 | 9/2007 | Simpson et al. |
| 2007/0215491 | A1 | 9/2007 | Heller et al. |
| 2007/0218097 | A1 | 9/2007 | Heller et al. |
| 2007/0227907 | A1 | 10/2007 | Shah et al. |
| 2007/0233013 | A1 | 10/2007 | Schoenberg |
| 2007/0244379 | A1 | 10/2007 | Boock et al. |
| 2007/0275193 | A1 | 11/2007 | DeSimone et al. |
| 2007/0299385 | A1 | 12/2007 | Santini et al. |
| 2007/0299409 | A1 | 12/2007 | Whitbourne et al. |
| 2008/0021008 | A1 | 1/2008 | Pacetti et al. |
| 2008/0027301 | A1 | 1/2008 | Ward et al. |
| 2008/0029391 | A1 | 2/2008 | Mao et al. |
| 2008/0033254 | A1 | 2/2008 | Kamath et al. |
| 2008/0033269 | A1 | 2/2008 | Zhang |
| 2008/0034972 | A1 | 2/2008 | Gough et al. |
| 2008/0045824 | A1 | 2/2008 | Tapsak et al. |
| 2008/0086040 | A1 | 4/2008 | Heller et al. |
| 2008/0086041 | A1 | 4/2008 | Heller et al. |
| 2008/0086043 | A1 | 4/2008 | Heller et al. |
| 2008/0091094 | A1 | 4/2008 | Heller et al. |
| 2008/0091095 | A1 | 4/2008 | Heller et al. |

FOREIGN PATENT DOCUMENTS

| | | |
|---|---|---|
| EP | 0 291 130 | 11/1988 |
| EP | 0 313 951 | 5/1989 |
| EP | 0 362 145 | 4/1990 |
| EP | 0 390 390 | 10/1990 |
| EP | 0 396 788 | 11/1990 |
| EP | 0 539 625 | 5/1993 |
| EP | 0 286 118 | 1/1995 |
| EP | 0 747 069 | 12/1996 |
| EP | 0 838 230 | 4/1998 |
| EP | 0 885 932 | 12/1998 |
| EP | 1 266 607 | 12/2002 |
| JP | 8196626 | 8/1966 |
| JP | 57156004 | 9/1982 |
| JP | 57156005 | 9/1982 |
| JP | 58163402 | 9/1983 |
| JP | 58163403 | 9/1983 |
| JP | 59029693 | 2/1984 |
| JP | 59049803 | 3/1984 |
| JP | 59049805 | 3/1984 |
| JP | 59059221 | 4/1984 |
| JP | 59087004 | 5/1984 |
| JP | 59209608 | 11/1984 |
| JP | 59209609 | 11/1984 |
| JP | 59209610 | 11/1984 |
| JP | 60245623 | 12/1985 |
| JP | 61238319 | 10/1986 |
| JP | 62074406 | 4/1987 |
| JP | 62102815 | 5/1987 |
| JP | 62227423 | 10/1987 |
| JP | 63130661 | 6/1988 |
| JP | 01018404 | 1/1989 |
| JP | 01018405 | 1/1989 |
| JP | 05279447 | 10/1993 |
| WO | WO 90/00738 | 1/1990 |
| WO | WO 92/07525 | 5/1992 |
| WO | WO 92/13271 | 8/1992 |
| WO | WO 93/19701 | 10/1993 |
| WO | WO 94/22367 | 10/1994 |
| WO | WO 96/01611 | 1/1996 |
| WO | WO 96/03117 | 2/1996 |
| WO | WO 96/14026 | 5/1996 |
| WO | WO 96/30431 | 10/1996 |
| WO | WO 96/32076 | 10/1996 |
| WO | WO 96/36296 | 11/1996 |
| WO | WO 97/11067 | 3/1997 |
| WO | WO 97/19188 | 5/1997 |
| WO | WO 99/13574 | 3/1999 |
| WO | WO 99/56613 | 4/1999 |
| WO | WO 99/48419 | 9/1999 |
| WO | WO 00/13003 | 3/2000 |
| WO | WO 00/19887 | 4/2000 |
| WO | WO 00/33065 | 6/2000 |
| WO | WO 01/12158 | 2/2001 |
| WO | WO 01/20019 | 3/2001 |
| WO | WO 01/43660 | 6/2001 |
| WO | WO 01/58348 | 8/2001 |
| WO | WO 01/68901 | 9/2001 |
| WO | WO 01/69222 | 9/2001 |
| WO | WO 01/88524 | 11/2001 |
| WO | WO 02/082989 | 10/2002 |
| WO | WO 03/022125 | 3/2003 |
| WO | WO 03/101862 | 12/2003 |
| WO | WO 2005/032400 | 4/2005 |
| WO | WO2005/044088 | 5/2005 |
| WO | WO 2006/018425 | 2/2006 |
| WO | WO 2006/122553 | 11/2006 |
| WO | WO 2007/114943 | 10/2007 |

OTHER PUBLICATIONS

International Search Report, dated Jul. 5, 2007.

Written Opinion of the International Searching Authority, dated Jul. 5, 2007.

Aalders et al. 1991. Development of a wearable glucose sensor; studies in healthy volunteers and in diabetic patients. The International Journal of Artificial Organs 14(2):102-108.

Abe et al. 1992. Characterization of glucose microsensors for intracellular measurements. Alan. Chem. 64(18):2160-2163.

Abel et al. 2002. Biosensors for in vivo glucose measurement: can we cross the experimental stage. Biosens Bioelectron 17:1059-1070.

Amin et al. 2003. Hypoglycemia prevalence in prepubertal children with type 1 diabetes on standard insulin regimen: Use of continuous glucose monitoring system. Diabetes Care 26(3):662-667.
Answers.com. "xenogenic." The American Heritage Stedman's Medical Dictionary. Houghton Mifflin Company, 2002. Answers. com Nov. 7, 2006 http://www. Answers.com/topic/xenogenic.
Armour et al. Dec. 1990. Application of Chronic Intravascular Blood Glucose Sensor in Dogs. Diabetes 39:1519-1526.
Asberg et al. 2003. Hydrogels of a Conducting Conjugated Polymer as 3-D Enzyme Electrode. Biosensors Bioelectronics. pp. 199-207.
Atanasov et al. 1994. Biosensor for continuous glucose monitoring. Biotechnology and Bioengineering 43:262-266.
Atanasov et al. 1997. Implantation of a refillable glucose monitoring-telemetry device. Biosens Bioelectron 12:669-680.
Bailey et al. 2007. Reduction in hemoglobin A1c with real-time continuous glucose monitoring: results from a 12-week observational study. Diabetes Technology & Therapeutics 9(3):203-210.
Beach et al. 1999. Subminiature implantable potentiostat and modified commercial telemetry device for remote glucose monitoring. IEEE Transactions on Instrumentation and Measurement 48(6):1239-1245.
Bindra et al. 1989. Pulsed amperometric detection of glucose in biological fluids at a surface-modified gold electrode. Anal Chem 61:2566-2570.
Bindra et al. 1991. Design and In Vitro Studies of a Needle-Type Glucose Senso for Subcutaneous Monitoring. Anal. Chem 63:1692-96.
Bisenberger et al. 1995. A triple-step potential waveform at enzyme multisensors with thick-film gold electrodes for detection of glucose and sucrose. Sensors and Actuators, B 28:181-189.
Bland et al. 1990. A note on the use of the intraclass correlation coefficient in the evaluation of agreement between two methods of measurement. Comput. Biol. Med. 20(5):337-340.
Bode et al. 1999. Continuous glucose monitoring used to adjust diabetes therapy improves glycosylated hemoglobin: A pilot study. Diabetes Research and Clinical Practice 46:183-190.
Bode et al. 2000. Using the continuous glucose monitoring system to improve the management of type 1 diabetes. Diabetes Technology & Therapeutics, 2(Suppl 1):S43-48.
Bode, B. W. 2000. Clinical utility of the continuous glucose monitoring system. Diabetes Technol Ther, 2(Suppl 1):S35-41.
Boland et al. 2001. Limitations of conventional methods of self-monitoring of blood glucose. Diabetes Care 24(11):1858-1862.
Bott, A. W. 1997. A Comparison of Cyclic Voltammetry and Cyclic Staircase Voltammetry Current Separations 16:1, 23-26.
Bowman, L.; Meindl, J. D. 1986. The packaging of implantable integrated sensors. IEEE Trans Biomed Eng BME33(2):248-255.
Brauker et al. 1995. Neovascularization of synthetic membranes directed by membrane Microarchitecture. J. Biomed Mater Res 29:1517-1524.
Brauker et al. 1998. Sustained expression of high levels of human factor IX from human cells implanted within an immunoisolation device into athymic rodents. Hum Gene Ther 9:879-888.
Brauker et al. 2001. Unraveling Mysteries at the Biointerface: Molecular Mediator of Inhibition of Blood vessel Formation in the Foreign Body Capsule Revealed. Surfacts Biomaterials 6. 1;5.
Brauker et al. Jun. 27, 1996. Local Inflammatory Response Around Diffusion Chambers Containing Xenografts Transplantation 61(12):1671-1677.
Bremer et al. 2001. Benchmark data from the literature for evaluation of new glucose sensing technologies. Diabetes Technology & Therapeutics 3(3):409-418.
Brooks et al. "Development of an on-line glucose sensor for fermentation monitoring," Biosensors, 3:45-56 (1987/88).
Bruckel et al. 1989. In vivo measurement of subcutaneous glucose concentrations with an enzymatic glucose sensor and a wick method. Klin Wochenschr 67:491-495.
Brunner et al. 1998. Validation of home blood glucose meters with respect to clinical and analytical approaches. Diabetes Care 21(4):585-590.
Cai et al. 2004. A wireless, remote query glucose biosensor based on a pH-sensitive polymer. Anal Chem 76(4):4038-4043.
Campanella et al. 1993. Biosensor for direct determination of glucose and lactate in undiluted biological fluids. Biosensors & Bioelectronics 8:307-314.
Cass et al. "Ferrocene-mediated enzyme electrodes for amperometric determination of glucose," Anal. Chem., 36:667-71 (1984).
Cellulose Acetate Product Description, Product No. 419028, Sigma-Aldrich Corp., St. Louis, MO. 2005.
Chase et al. 2001. Continuous subcutaneous glucose monitoring in children with type 1 diabetes. Pediatrics 107:222-226.
Chen et al. 2006. A noninterference polypyrrole glucose biosensor. Biosensors and Bioelectronics 22:639-643.
Ciba® Irgacure 2959 Photoinitiator Product Description, Ciba Specialty Chemicals Inc., Basel, Switzerland.
Claremont et al. 1986. Subcutaneous implantation of a ferrocene-mediated glucose sensor in pigs. Diabetologia 29:817-821.
Claremont et al. Jul. 1986. Potentially-impintable, ferrocene-mediated glucose sensor. J. Biomed. Eng. 8:272-274.
Clark et al. 1988. Long-term stability of electroenzymatic glucose sensors implanted in mice. Trans Am Soc Artif Intern Organs 34:259-265.
Colowick et al. 1976. Methods in Enzymlology, vol. XLIV, Immobilized Enzymes. New York: Academic Press.
Cox et al. 1985. Accuracy of perceiving blood glucose in IDDM. Diabetes Care 8(6):529-536.
Csoregi et al., 1994. Design, characterization, and one-point in vivo calibration of a subcutaneously implanted glucose electrode. Anal Chem. 66(19):3131-3138.
Dai et al. 1999. Hydrogel Membranes with Mesh Size Asymmetry Based on the Gradient Crosslink of Poly(vinyl alcohol). Journal of Membrane Science 156:67-79.
D'Arrigo et al. 2003. Porous-Si based bioreactors for glucose monitoring and drugs production. Proc. of SPIE 4982:178-184.
Direct 30/30® meter (Markwell Medical) (Catalog).
Dixon et al. 2002. Characterization in vitro and in vivo of the oxygen dependence of an enzyme/polymer biosensor for monitoring brain glucose. Journal of Neuroscience Methods 119:135-142.
DuPont[1] Dimension AR® (Catalog).
Edwards Lifesciences. Accuracy for your and your patients. Marketing materials, 4 pp. 2002.
El Deheigy et al. 1986. Optimization of an implantable coated wire glucose sensor. J. Biomed Eng. 8: 121-129.
El-Khatib et al. 2007. Adaptive closed-loop control provides blood-glucose regulation using dual subcutaneous insulin and glucagon infusion in diabetic swine, Journal of Diabetes Science and Technology, 1(2):181-192.
El-Sa'ad et al. 1990. Moisture Absorption by Epoxy Resins: the Reverse Thermal Effect. Journal of Materials Science 25:3577-3582.
Ernst et al. 2002. Reliable glucose monitoring through the use of microsystem technology. Anal. Bioanal. Chem. 373:758-761.
Fare et al. 1998. Functional characterization of a conducting polymer-based immunoassay system. Biosensors & Bioelectronics 13(3-4):459-470.
Feldman et al. 2003. A continuous glucose sensor based on wired enzyme technology—results from a 3-day trial in patients with type 1 diabetes. Diabetes Technol Ther 5(5):769-779.
Fischer et al. 1989. Oxygen Tension at the Subcutaneous Implantation Site of Glucose Sensors. Biomed. Biochem 11/12:965-972.
Frohnauer et al. 2001. Graphical human insulin time-activity profiles using standardized definitions. Diabetes Technology & Therapeutics 3(3):419-429.
Frost et al. 2002. Implantable chemical sensors for real-time clinical monitoring: Progress and challenges. Current Opinion in Chemical Biology 6:633-641.
Garg et al. 2004. Improved Glucose Excursions Using an Implantable Real-Time continuous Glucose Sensor in Adults with Type I Diabetes. Diabetes Care 27:734-738.
Geller et al. 1997. Use of an immunoisolation device for cell transplantation and tumor immunotherapy. Ann NY Acad Sci 831:438-451.
Gerritsen et al. 1999. Performance of subcutaneously implanted glucose sensors for continuous monitoring. The Netherlands Journal of Medicine 54:167-179.

Gerritsen et al. 2001. Influence of inflammatory cells and serum on the performance of implantable glucose sensors. J Biomed Mater Res 54:69-75.
Gerritsen, M. 2000. Problems associated with subcutaneously implanted glucose sensors. Diabetes Care 23(2):143-145.
Gilligan et al. 1994. Evaluation of a subcutaneous glucose sensor out to 3 months in a dog model. Diabetes Care 17(8):882-887.
Gilligan et al. 2004, Feasibility of continuous long-term glucose monitoring from a subcutaneous glucose sensor in humans. Diabetes Technol Ther 6:378-386.
Godsland et al. 2001. Maximizing the Success Rate of Minimal Model Insulin Sensitivity Measurement in Humans: The Importance of Basal Glucose Levels. The Biochemical Society and the Medical Research Society, 1-9.
Gough et al. 2000. Immobilized glucose oxidase in implantable glucose sensor technology. Diabetes Technology & Therapeutics 2(3):377-380.
Gough et al. 2003. Frequency characterization of blood glucose dynamics. Annals of Biomedical Engineering 31:91-97.
Gregg et al. 1990. Cross-Linked Redox Gels Containing Glucose Oxidase for Amperometric Biosensor Applications. Anal. Chem. 62:258-263.
Gross et al. 2000. Efficacy and reliability of the continuous glucose monitoring system. Diabetes Technology & Therapeutics, 2(Suppl 1):S19-26.
Gross et al. 2000. Performance evaluation of the MiniMed® continuous glucose monitoring system during patient home use. Diabetes Technology & Therapeutics 2(1):49-56.
Hall et al. 1998. Electrochemical oxidation of hydrogen peroxide at platinum electrodes. Part II: Effect of potential. Electrochimica Acta 43(14-15):2015-2024.
Hall et al. 1998. Electrochemical oxidation of hydrogen peroxide at platinum electrodes. Part I: An adsorption-controlled mechanism. Electrochimica Acta, 43(5-6):579-588.
Hall et al. 1999. Electrochemical oxidation of hydrogen peroxide at platinum electrodes. Part III: Effect of temperature. Electrochimica Acta, 44:2455-2462.
Hall et al. 1999. Electrochemical oxidation of hydrogen peroxide at platinum electrodes. Part IV: Phosphate buffer dependence. Electrochimica Acta, 44:4573-4582.
Hall et al. 2000. Electrochemical oxidation of hydrogen peroxide at platinum electrodes. Part V: Inhibition by chloride. Electrochimica Acta, 45:3573-3579.
Harrison et al. 1988. Characterization of perfluorosulfonic acid polymer coated enzyme electrodes and a miniaturized integrated potentiostat for glucose analysis in whole blood. Anal. Chem. 60:2002-2007.
Heller, A. 1992. Electrical Connection of Enzyme Redox Centers to Electrodes. J. Phys. Chem. 96:3579-3587.
Heller, A. 1999. Implanted electrochemical glucose sensors for the management of diabetes. Annu Rev Biomed Eng 1:153-175.
Heller, A. 2003. Plugging metal connectors into enzymes. Nat Biotechnol 21:631-2.
Hitchman, M. L. 1978. Measurement of Dissolved Oxygen. In Elving et al. (Eds.). Chemical Analysis, vol. 49, Chap. 3, pp. 34-49, 59-123. New York: John Wiley & Sons.
Hrapovic et al. 2003. Picoamperometric detection of glucose at ultrasmall platinum-based biosensors: preparation and characterization. Anal Chem 75:3308-3315.
Huang et al. A 0.5mV passive telemetry IC for biomedical applications. Swiss Federal Institute of Technology. 4 pp.
Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode, pp. 1-116.
Hunter, I., Jones, L., Kanigan, T., Brenan, C., Sanbol, L. Sosnowski, L. 2000. Minimally Invasive Glucose Sensor and Insulin Delivery System. MIT Home Automation and Healthcare Consortium. Progress Report No. 25.
Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Complications, 12:295-301.
Jensen et al. 1997. Fast wave forms for pulsed electrochemical detection of glucose by incorporation of reductive desorption of oxidation products. Analytical Chemistry 69(9):1776-1781.
Jeutter, D. C. 1982. A transcutaneous implanted battery recharging and biotelemeter power switching system. IEEE Trans Biomed Eng 29:314-321.
Johnson et al. 1992. In vivo evaluation of an electroenzymatic glucose sensor implanted in subcutaneous tissue. Biosensors & Bioelectronics, 7:709-714.
Jovanovic, L. 2000. The role of continuous glucose monitoring in gestational diabetes mellitus. Diabetes Technology & Therapeutics, 2 Suppl 1, S67-71.
Kang et al. 2003. In vitro and short-term in vivo characteristics of a Kel-F thin film modified glucose sensor. Anal Sci 19:1481-1486.
Kargol et al. 2001. Studies on the structural properties of porous membranes: measurement of linear dimensions of solutes. Biophys Chem 91:263-271.
Karube et al. 1993. Microbiosensors for acetylcholine and glucose. Biosensors & Bioelectronics 8:219-228.
Kaufman et al. 2001. A pilot study of the continuous glucose monitoring system. Diabetes Care 24(12):2030-2034.
Kaufman. 2000. Role of the continuous glucose monitoring system in pediatric patients. Diabetes Technology & Therapeutics 2(1):S-49-S-52.
Kerner et al. "The function of a hydrogen peroxide-detecting electroenzymatic glucose electrode is markedly impaired in human sub-cutaneous tissue and plasma," Biosensors & Bioelectronics, 8:473-482 (1993).
Kerner et al. 1988. A potentially implantable enzyme electrode for amperometric measurement of glucose, Horm Metab Res Suppl. 20:8-13.
Kiechle, F.L. 2001. The impact of continuous glucose monitoring on hospital point-of-care testing programs. Diabetes Technol Ther 3:647-649.
Klueh et al. 2003. Use of Vascular Endothelia Cell Growth Factor Gene Transfer To Enhance Implantable Sensor Function in Vivo, Biosensor Function and Vegf-Gene Transfer, pp. 1072-1086.
Klueh et al. 2007. Inflammation and glucose sensors: use of dexamethasone to extend glucose sensor function and life span in vivo. Journal of Diabetes Science and Technology 1(4):496-504.
Kondo et al. 1982. A miniature glucose sensor, implantable in the blood stream. Diabetes Care. 5(3):218-221.
Koschinsky et al. 1998. New approach to technical and clinical evaluation of devices for self-monitoring of blood glucose. Diabetes Care 11(8): 619-619.
Koschinsky et al. 2001. Sensors for glucose monitoring: Technical and clinical aspects. Diabetes Metab. Res. Rev. 17:113-123.
Koudelka et al. 1989. In vivo response of microfabricated glucose sensors to glycemia changes in normal rats. Biomed Biochim Acta 48(11-12):953-956.
Koudelka et al. 1991. In-vivo behaviour of hypodermically implanted microfabricated glucose sensors. Biosensors & Bioelectronics 6:31-36.
Kraver et al. 2001. A mixed-signal sensor interface microinstrument. Sensors and Actuators A 91:266-277.
Kruger et al. 2000. Psychological motivation and patient education: A role for continuous glucose monitoring. Diabetes Technology & Therapeutics, 2(Suppl 1):S93-97.
Kunzler et al. 1993. Hydrogels based on hydrophilic side chain siloxanes. Poly Mat Sci and Eng 69:226-227.
Kunzler et al. Aug. 21, 1995. Contact lens materials. Chemistry & Industry. 651-655.
Kurtz et al. 2005. Recommendations for blood pressure measurement in humans and experimental animals, Part 2: Blood pressure measurement in experimental animals, A statement for professionals from the subcommittee of professional and public education of the American Heart Association Council on High Blood Pressure Research. Hypertension 45:299-310.

Lee et al. 1999. Effects of pore size, void volume, and pore connectivity on tissue responses. Society for Biomaterials 25th Annual Meeting, 171.
Lerner et al. 1984. An implantable electrochemical glucose sensor. Ann. N. Y. Acad. Sci. 428:263-278.
Lewandowski et al. 1988. Evaluation of a miniature blood glucose sensor. Trans Am Soc Artif Intern Organs 34:255-258.
Leypoldt et al. 1984. Model of a two-substrate enzyme electrode for glucose. Anal. Chem. 56:2896-2904.
Linke et al. 1994. Amperometric biosensor for in vivo glucose sensing based on glucose oxidase immobilized in a redox hydrogel. Biosensors & Bioelectronics 9:151-158.
Loffler et al. 1995. Separation and determination of traces of ammonia in air by means of chromatomembrane cells. Fresenius J Anal Chem 352:613-614.
Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.
Lyman D. 1960. Polyurethanes. I. The Solution Polymerization of Diisocyanates with Ethylene Glycol. J. Polymer Sci XLV:45:49.
Madaras et al. 1996. Microfabricated amperometric creatine and creatinine biosensors. Analytica Chimica Acta 319:335-345.
Makale et al. 2003. Tissue window chamber system for validation of implanted oxygen sensors. Am. J. Physiol. Heart Circ. Physiol. 284:H2288-2294.
Malin et al. 1999. Noninvasive Prediction of Glucose by Near-Infrared Diffuse Reflectance Spectroscopy. Clinical Chemistry 45:9, 1651-1658.
Maran et al. 2002. Continuous subcutaneous glucose monitoring in diabetic patients: A multicenter analysis. Diabetes Care 25(2):347-352.
March, W. F. 2002. Dealing with the delay. Diabetes Technol Ther 4(1):49-50.
Mastrototaro et al. "An electroenzymatic glucose sensor fabricated on a flexible substrate," Sensors and Actuators B, 5:139-44 (1991).
Mastrototaro et al. 2003. Reproducibility of the continuous glucose monitoring system matches previous reports and the intended use of the product. Diabetes Care 26:256; author reply p. 257.
Mastrototaro, J. J. 2000. The MiniMed continuous glucose monitoring system. Diabetes Technol Ther 2(Suppl 1):S13-8.
Matsumoto et al. 1998. A micro-planar amperometeric glucose sensor unsusceptible to interference species. Sensors and Actuators B 49:68-72.
Matsumoto et al. 2001. A long-term lifetime amperometric glucose sensor with a perfluorocarbon polymer coating. Biosens Bioelectron 16:271-276.
Matthews et al. 1988. An amperometric needle-type glucose sensor testing in rats and man. Diabetic Medicine 5:248-252.
McCartney et al. 2001. Near-infrared fluorescence lifetime assay for serum glucose based on allophycocyanin-labeled concanavalin A. Anal Biochem 292:216-221.
McGrath et al. 1995. The use of differential measurements with a glucose biosensor for interference compensation during glucose determinations by flow injection analysis. Biosens Bioelectron 10:937-943.
McKean, et al. Jul. 7, 1988. A Telemetry Instrumentation System for Chronically Implanted Glucose and Oxygen Sensors. Transactions on Biomedical Engineering 35:526-532.
Memoli et al. 2002. A comparison between different immobilised glucoseoxidase-based electrodes. J Pharm Biomed Anal 29:1045-1052.
Merriam-Webster Online Dictionary. The term "nominal." http://www.m-w.com/dictionary/nominal.
Meyerhoff et al. 1992. On line continuous monitoring of subcutaneous tissue glucose in men by combining portable glucosensor with microdialysis. Diabetologia 35:1087-1092.
Miller et al. 1989. In vitro stimulation of fibroblast activity by factors generated from human monocytes activated by biomedical polymers. Journal of J Biomed Mater Res 23:911-930.
Miller et al. 1989. Generation of IL1-like activity in response to biomedical polymer implants: a comparison of in vitro and in vivo models. J Biomed Mater Res 23:1007-1026.
Miller, A. 1988. Human monocyte/macrophage activation and interleukin 1 generation by biomedical polymers. J Biomed Mater Res 23:713-731.
Moatti-Sirat et al. 1992. Towards continuous glucose monitoring: in vivo evaluation of a miniaturized glucose sensor implanted for several days in rat subcutaneous tissue. Diabetologia 35:224-230.
Moatti-Sirat, D et al. 1992. Evaluating in vitro and in vivo the interference of ascorbate and acetaminophen on glucose detection by a needle-type glucose sensor. Biosensors and Bioelectronics 7:345-352.
Moussy et al. 2000. Biomaterials community examines biosensor biocompatibility Diabetes Technol Ther 2:473-477.
Mowery et al. 2000. Preparation and characterization of hydrophobic polymeric films that are thromboresistant via nitric oxide release. Biomaterials 21:9-21.
Muslu. 1991. Trickling filter performance. Apllied Biochemistry and Biotechnology 37:211-224.
Myler et al. 2002. Ultra-thin-polysiloxane-film-composite membranes for the optimisation of amperometric oxidase enzyme electrodes. Biosens Bioelectron 17:35-43.
Nafion® 117 Solution Product Description, Product No. 70160, Sigma-Aldrich Corp., St. Louis, MO.
Nakayama et al. 1992. Surface fixation of hydrogels: heparin and glucose oxidase hydrogelated surfaces. ASAIO Journal M421-M424.
Nam et al. 2000. A novel fabrication method of macroporous biodegradable polymer scaffolds using gas foaming salt as a porogen additive. J Biomed Mater Res 53:1-7.
Ohara et al. 1994. "Wired" enzyme electrodes for amperometric determination of glucose or lactate in the presence of interfering substances. Anal Chem 66:2451-2457.
Okuda et al. 1971. Mutarotase effect on micro determinations of D-glucose and its anomers with β-D-glucose oxidase. Anal Biochem 43:312-315.
Palmisano et al. 2000. Simultaneous monitoring of glucose and lactate by an interference and cross-talk free dual electrode amperometric biosensor based on electropolymerized thin films. Biosensors & Bioelectronics 15:531-539.
Panetti 2002. Differential effects of sphingosine 1-phosphate and lysophosphatidic acid on endothelial cells. Biochimica et Biophysica Acta 1582:190-196.
Patel et al. 2003. Amperometric glucose sensors based on ferrocene containing polymeric electron transfer systems-a preliminary report. Biosens Bioelectron 18:1073-6.
Pegoraro et al. 1995. Gas transport properties of siloxane polyurethanes, Journal of Applied Polymer Science 57(421-429).
Pfeiffer et al. 1992. On line continuous monitoring of subcutaneous tissue glucose is feasible by combining portable glucosensor with microdialysis. Horm. Metab. Res. 25:121-124.
Pfeiffer, E.F. The glucose sensor: the missing link in diabetes therapy. 154-164.
Phillips and Smith. 1988. Bromedical Applications of Polyurethanes: Implications of Failure Mechanisms. J. Biomat. Appl. 3:202-227.
Pichert et al. 2000. Issues for the coming age of continuous glucose monitoring Diabetes Educ 26(6):969-980.
Pickup et al. "Implantable glucose sensors: choosing the appropriate sensor strategy," Biosensors, 3:335-346 (1987/88).
Pickup et al. 1988. Progress towards in vivo glucose sensing with a ferrocene-mediated amperometric enzyme electrode. 34-36.
Pickup et al. "In vivo molecular sensing in diabetes mellitus: an implantable glucose sensor with direct electron transfer," Diabetologia, 32:213-217 (1989).
Pickup et al. 1989. Potentially-implantable, amperometric glucose sensors with mediated electron transfer: improving the operating stability. Biosensors 4:109-119.
Pineda et al. 1996. Bone regeneration with resorbable polymeric membranes. III. Effect of poly(L-lactide) membrane pore size on the bone healing process in large defects. J. Biomedical Materials Research 31:385-394.
Pishko et al. "Amperometric glucose microelectrodes prepared through immobilization of glucose oxidase in redox hydrogels," Anal. Chem., 63:2268-72 (1991).

Pitzer et al. 2001. Detection of hypoglycemia with the GlucoWatch biographer. Diabetes Care 24(5):881-885.
Poitout et al. 1993. A glucose monitoring system for on line estimation in man of blood glucose concentration using a miniaturized glucose sensor implanted in the subcutaneous tissue and a wearable control unit. Diabetologia 36:658-663.
Poitout et al. 1994. Development of a glucose sensor for glucose monitoring in man: the disposable implant concept. Clinical Materials 15:241-246.
Postlethwaite et al. 1996. Interdigitated array electrode as an alternative to the rotated ring-disk electrode for determination of the reaction products of dioxygen reduction. Analytical Chemistry 68:2951-2958.
Quinn et al. 1995. Kinetics of glucose delivery to subcutaneous tissue in rats measured with 0.3-mm amperometric microsensors. The American Physiological Society E155-E161.
Quinn et al. 1997. Biocompatible, glucose-permeable hydrogel for in situ coating of implantable biosensors. Biomaterials 18:1665-1670.
Ratner, B.D. 2002. Reducing capsular thickness and enhancing angiogenesis around implant drug release systems. J Control Release 78:211-218.
Reach et al. 1986. A Method for Evaluating in vivo the Functional Characteristics of Glucose Sensors. Biosensors 2:211-220.
Reach, G. 2001. Which threshold to detect hypoglycemia? Value of receiver-operator curve analysis to find a compromise between sensitivity and specificity. Diabetes Care 24(5):803-804.
Reach, Gerard. 2001. Letters to the Editor Re: Diabetes Technology & Therapeutics, 2000;2:49-56. Diabetes Technology & Therapeutics 3(1):129-130.
Rebrin et al. "Automated feedback control of subcutaneous glucose concentration in diabetic dogs," Diabetologia, 32:573-76 (1989).
Rebrin et al. 1992. Subcutaenous glucose monitoring by means of electrochemical sensors: fiction or reality? J. Biomed. Eng. 14:33-40.
Rhodes et al. 1994. Prediction of pocket-portable and implantable glucose enzyme electrode performance from combined species permeability and digital simulation analysis. Analytical Chemistry 66(9):1520-1529.
Sachlos et al. 2003. Making Tissue Engineering Scaffolds Work. Review on the Application of Sold Freeform Fabrication Technology to the Production of Tissue Engineering Scaffolds. European Cells and Materials 5:29-40.
Sakakida et al. 1992. Development of Ferrocene-Mediated Needle-Type Glucose Sensor as a Measure of True Subcutaneous Tissue Glucose Concentrations. Artif. Organs Today 2(2):145-158.
Sakakida et al. 1993. Ferrocene-Mediated Needle Type Glucose Sensor Covered with Newly Designed Biocompatible Membran, Sensors and Actuators B 13-14:319-322.
Salardi et al. 2002. The glucose area under the profiles obtained with continuous glucose monitoring system relationships with HbA1c in pediatric type 1 diabetic patients. Diabetes Care 25(10)1840-1844.
Sanders et al. 2003. Fibrous Encapsulation of Single Polymer Microfibers Depends on their Vertical Dimension in subcutaneous Tissue Polymer Microfibers pp. 1181-1187.
Sansen et al. 1985. "Glucose sensor with telemetry system." In Ko, W. H. (Ed.). Implantable Sensors for Closed Loop Prosthetic Systems. Chap. 12, pp. 167-175, Mount Kisco, NY: Futura Publishing Co.
Sansen et al. 1990. A smart sensor for the voltammetric measurement of oxygen or glucose concentrations. Sensors and Actuators B 1:298-302.
Schmidt et al. 1993. Glucose concentration in subcutaneous extracellular space. Diabetes Care 16(5):695-700.
Schoemaker et al. 2003. The SCGM1 system: Subcutaneous continuous glucose monitoring based on microdialysis technique. Diabetes Technology & Therapeutics 5(4):599-608.
Schoonen et al. 1990 Development of a potentially wearable glucose sensor for patients with diabetes mellitus: design and in-vitro evaluation. Biosensors & Bioelectronics 5:37-46.
Schuler et al. 1999. Modified gas-permeable silicone rubber membranes for covalent immobilisation of enzymes and their use in biosensor development. Analyst 124:1181-1184.
Selam, J. L. 1997. Management of diabetes with glucose sensors and implantable insulin pumps. From the dream of the 60s to the realities of the 90s. ASAIO J, 43:137-142.
Service, R. F. 2002. Can sensors make a home in the body? Science 297:962-3.
Shaw et al. "In vitro testing of a simply constructed, highly stable glucose sensor suitable for implantation in diabetic patients," Biosensors & Bioelectronics, 6:401-406 (1991).
Shichiri et al. 1982. Wearable artificial endocrine pancrease with needle-type glucose sensor. Lancet 2:1129-1131.
Shichiri et al. 1983. Glycaemic Control in Pancreatectomized Dogs with a Wearable Artificial Endocrine Pancreas. Diabetologia 24:179-184.
Shichiri et al. 1985. Needle-type Glucose Sensor for Wearable Artificial Endocrine Pancreas in Implantable Sensors 197-210.
Shichiri et al., 1989. Membrane Design For Extending the Long-Life of an Implantable Glucose Sensor. Diab. Nutr. Metab. 2:309-313.
Shults et al. 1994. A telemetry-instrumentation system for monitoring multiple subcutaneously implanted glucose sensors. IEEE Transactions on Biomedical Engineering 41(10):937-942.
Sieminski et al. 2000. Biomaterial-microvasculature interactions. Biomaterials 21:2233-2241.
Skyler, J. S. 2000. The economic burden of diabetes and the benefits of improved glycemic control: The potential role of a continuous glucose monitoring system. Diabetes Technology & Therapeutics 2 Suppl 1:S7-12.
Sokol et al. 1980, Immobilized-enzyme rate-determination method for glucose analysis, Clin. Chem. 26(1):89-92.
Sriyudthsak et al. 1996. Enzyme-epoxy membrane based glucose analyzing system and medical applications. Biosens Bioelectron 11:735-742.
Steil et al. 2003. Determination of plasma glucose during rapid glucose excursions with a subcutaneous glucose sensor. Diabetes Technology & Therapeutics 5(1):27-31.
Sternberg et al. 1988. Study and Development of Multilayer Needle-type Enzyme-based Glucose Microsensors. Biosensors 4:27-40.
Sternberg et al. 1988. Covalent enzyme coupling on cellulose acetate membranes for glucose sensor development. Anal. Chem. 69:2781-2786.
Stokes. 1988. Polyether Polyurethanes: Biostable or Not? J. Biomat. Appl. 3:228-259.
Suh et al. 2002. Behavior of fibroblasts on a porous hyaluronic acid incorporated collagen matrix. Yonsei Medical Journal 43(2):193-202.
Sumino T. et al. 1998. Preliminary study of continuous glucose monitoring with a microdialysis technique. Proceedings of the IEEE, 20(4):1775-1778.
Takegami et al. 1992. Pervaporation of ethanol water mixtures using novel hydrophobic membranes containing polydimethylsiloxane, Journal of Membrance Science, 75(93-105).
Tanenberg et al. 2000. Continuous glucose monitoring system: A new approach to the diagnosis of diabetic gastroparesis. Diabetes Technology & Therapeutics, 2 Suppl 1:S73-80.
Tang et al. 1993. Fibrin(ogen) mediates acute inflammatory responses to biomaterials. J Exp Med 178:2147-2156.
Tang et al. 1995. Inflammatory responses to biomaterials. Am J Clin Pathol 103:466-471.
Tang et al. 1996. Molecular determinants of acute inflammatory responses to biomaterials. J Clin Invest 97:1329-1334.
Tang et al. 1998. Mast cells mediate acute inflammatory responses to implanted biomaterials. Proc Natl Acad Sci U S A 95:8841-8846.
Thomé-Duret et al. 1996. Modification of the sensitivity of glucose sensor implanted into subcutaneous tissue. Diabetes Metabolism, 22:174-178.
Thomé-Duret et al. 1998. Continuous glucose monitoring in the free-moving rat. Metabolism, 47:799-803.
Thompson et al., In Vivo Probes: Problems and Perspectives, Department of Chemistry, University of Toronto, Canada, pp. 255-261, 1986.
Tibell et al. 2001. Survival of macroencapsulated allogeneic parathyroid tissue one year after transplantation in nonimmunosuppressed humans. Cell Transplant 10:591-9.
Tierney et al. 2000. Effect of acetaminophen on the accuracy of glucose measurements obtained with the GlucoWatch biographer. Diabetes Technol Ther 2:199-207.

Tierney et al. 2000. The GlucoWatch® biographer: A frequent, automatic and noninvasive glucose monitor. Ann. Med. 32:632-641.
Trecroci, D. 2002. A Glimpse into the Future- Continuous Monitoring of Glucose with a Microfiber. Diabetes Interview 42-43.
Tse and Gough. 1987. Time-Dependent Inactivation of Immobilized Glucose Oxidase and Catalase. Biotechnol. Bioeng. 29:705-713.
Turner and Pickup, "Diabetes mellitus: biosensors for research and management," *Biosensors*, 1:85-115 (1985).
Turner, A.P.F. 1988. Amperometric biosensor based on mediator-modified electrodes. Methods in Enzymology 137:90-103.
Unger et al. 2004. Glucose control in the hospitalized patient. Emerg Med 36(9), 12 pp.
Updike et al. 1967. The enzyme electrode. Nature, 214:986-988.
Updike et al. 1988. Laboratory Evaluation of New Reusable Blood Glucose Sensor. Diabetes Care, 11:801-807.
Updike et al. 1994. Enzymatic glucose sensor: Improved long-term performance in vitro and in vivo. ASAIO Journal, 40(2):157-163.
Updike et al. 1997. Principles of long-term fully impleated sensors with emphasis on radiotelemetric monitoring of blood glucose form inside a subcutaneous foreign body capsule (FBC). In Fraser, ed., Biosensors in the Body. New York. John Wiley & Sons, pp. 117-137.
Updike et al. 2000. A subcutaneous glucose sensor with improved longevity, dynamic range, and stability of calibration. Diabetes Care 23(2):208-214.
Utah Medical Products Inc., Blood Pressure Tranducers product specifications. 6 pp. 2003-2006, 2003.
Vadgama, P. Nov. 1981. Enzyme electrodes as practical biosensors. Journal of Medical Engineering & Technology 5(6):293-298.
Van den Berghe 2004. Tight blood glucose control with insulin in "real-life" intensive care. Mayo Clin Proc 79(8):977-978.
Velho et al. 1989. In vitro and in vivo stability of electrode potentials in needle-type glucose sensors. Influence of needle material. Diabetes 38:164-171.
Wade Jr., L.G. Organic Chemistry, Chapter 17, Reactions of Aromatic Compounds pp. 762-763, 2003.
Wagner et al. 1998. Continuous amperometric monitoring of glucose in a brittle diabetic chimpanzee with a miniature subcutaneous electrode. Proc. Natl. Acad. Sci. A, 95:6379-6382.
Wang et al. 1994. Highly Selective Membrane-Free, Mediator-Free Glucose Biosensor. Anal. Chem. 66:3600-3603.
Wang et al. 1997. Improved ruggedness for membrane-based amperometric sensors using a pulsed amperometric method. Anal Chem 69:4482-4489.
Ward et al. 2000. Understanding Spontaneous Output Fluctuations of an Amperometric Glucose Sensor: Effect of Inhalation Anesthesia and e of a Nonenzyme Containing Electrode. ASAIO Journal 540-546.
Ward et al. 2000. Rise in background current over time in a subcutaneous glucose sensor in the rabbit: Relevance to calibration and accuracy. Biosensors & Bioelectronics, 15:53-61.
Ward et al. 2002. A new amperometric glucose microsensor: in vitro and short-term in vivo evaluation. Biosensors & Bioelectronics, 17:181-189.
Wientjes, K. J. C. 2000. Development of a glucose sensor for diabetic patients (Ph.D. Thesis).
Wilkins et al. 1995. Glucose monitoring: state of the art and future possibilities. Med Eng Phys 18:273-288.
Wilkins et al. 1995. Integrated implantable device for long-term glucose monitoring. Biosens. Bioelectron 10:485-494.
Wilkins et al. 1988. The coated wire electrode glucose sensor, Horm Metab Res Suppl., 20:50-55.
Wilson et al. 1992. Progress toward the development of an implantable sensor for glucose. Clin. Chem. 38(9):1613-1617.
Wilson et al. 2000. Enzyme-based biosensors for in vivo measurements. Chem. Rev., 100:2693-2704.
Wood, W. et al. Mar. 1990. Hermetic Sealing with Epoxy. Mechanical Engineering 1-3.
Woodward. 1982. How Fibroblasts and Giant Cells Encapsulate Implants: Considerations in Design of Glucose Sensor. Diabetes Care 5:278-281.
Wu et al. 1999. In site electrochemical oxygen generation with an immunoisolation device. Annals New York Academy of Sciences, pp. 105-125.
Yamasaki et al. 1989. Direct measurement of whole blood glucose by a needle-type sensor. Clinica Chimica Acta. 93:93-98.
Yamasaki, Yoshimitsu. Sep. 1984. The development of a needle-type glucose sensor for wearable artificial endocrine pancreas. Medical Journal of Osaka University 35(1-2):25-34.
Yang et al. 1998. Development of needle-type glucose sensor with high selectivity. Science and Actuators B 46:249-256.
Yang, et al. 2004. A Comparison of Physical Properties and Fuel Cell Performance of Nafion and Zirconium Phosphate/Nafion Composite Membranes. Journal Of Membrane Science 237:145-161.
Zamzow et al. Development and evaluation of a wearable blood glucose monitor. pp. M588-M591, 1990.
Zhang et al. 1994. Elimination of the acetaminophen interference in an implantable glucose sensor. Analytical Chemistry 66(7):1183-1188.
Office Action dated Oct. 5, 2007 in U.S. Appl. No. 10/896,639.
Office Action dated Apr. 11, 2007 in U.S. Appl. No. 10/896,639.
Office Action dated Aug. 22, 2006 in U.S. Appl. No. 10/896,639.
Office Action dated Apr. 6, 2006 in U.S. Appl. No. 10/896,639.
Office Action dated Sep. 23, 2005 in U.S. Appl. No. 10/896,639.
Office Action dated Dec. 3, 2008 in U.S. Appl. No. 11/675,063.
Office Action dated Mar. 14, 2007 in U.S. Appl. No. 10/695,636.
Office Action dated May 22, 2006 in U.S. Appl. No. 10/695,636.
Office Action dated Dec. 6, 2005 in U.S. Appl. No. 10/695,636.
IPRP for PCT/US06/14127 filed Apr. 14, 2006.

* cited by examiner

SILICONE BASED MEMBRANES FOR USE IN IMPLANTABLE GLUCOSE SENSORS

RELATED APPLICATION

This Application is related to U.S. application Ser. No. 11/404,418, entitled "SILICONE BASED MEMBRANES FOR USE IN IMPLANTABLE GLUCOSE SENSORS," filed on even date herewith, which is incorporated herein by reference in its entirety.

FIELD OF THE INVENTION

The invention relates to membranes for use in implantable analyte sensors (e.g., glucose sensors).

BACKGROUND OF THE INVENTION

Electrochemical sensors are useful in chemistry and medicine to determine the presence or concentration of a biological analyte. Such sensors are useful, for example, to monitor glucose in diabetic patients and lactate during critical care events.

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) is induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically utilizes uncomfortable finger pricking methods. Due to the lack of comfort and convenience, a diabetic normally only measures his or her glucose level two to four times per day. Unfortunately, these time intervals are spread so far apart that the diabetic likely finds out too late, sometimes incurring dangerous side effects, of a hyperglycemic or hypoglycemic condition. In fact, it is not only unlikely that a diabetic will take a timely SMBG value, but additionally the diabetic will not know if their blood glucose value is going up (higher) or down (lower) based on conventional methods.

Consequently, a variety of transdermal and implantable electrochemical sensors are being developed for continuously detecting and/or quantifying blood glucose values. Many implantable glucose sensors suffer from complications within the body and provide only short-term or less-than-accurate sensing of blood glucose. Similarly, transdermal sensors have problems in accurately sensing and reporting back glucose values continuously over extended periods of time. Some efforts have been made to obtain blood glucose data from implantable devices and retrospectively determine blood glucose trends for analysis; however these efforts do not aid the diabetic in determining real-time blood glucose information. Some efforts have also been made to obtain blood glucose data from transdermal devices for prospective data analysis, however similar problems have been observed.

SUMMARY OF THE INVENTION

One embodiment disclosed herein includes a membrane for use in an analyte sensor, the membrane including a silicone elastomer and a poly(ethylene oxide) and poly(propylene oxide) co-polymer, wherein the membrane is adapted to permit diffusion of both the analyte and oxygen therethrough. In one embodiment, the silicone elastomer is a dimethyl- and methylhydrogen-siloxane copolymer. In one embodiment, the silicone elastomer comprises vinyl substituents. In one embodiment, the silicone elastomer is an elastomer produced by curing a MED-4840 mixture. In one embodiment, the copolymer comprises hydroxy substituents. In one embodiment, the co-polymer is a triblock poly(ethylene oxide)-poly(propylene oxide)-poly(ethylene oxide) polymer. In one embodiment, the co-polymer is a triblock poly(propylene oxide)-poly(ethylene oxide)-poly(propylene oxide) polymer. In one embodiment, the co-polymer is a PLURONIC® polymer. In one embodiment, the co-polymer is PLURONIC® F-127. In one embodiment, the analyte is glucose. In one embodiment, at least a portion of the co-polymer is cross-linked. In one embodiment, from about 5% w/w to about 30% w/w of the membrane is the co-polymer.

Another embodiment disclosed herein includes an implantable analyte sensor having an enzyme layer comprising an enzyme for which the analyte is a substrate and a bioprotective layer positioned between the enzyme layer and tissue adjacent to the sensor when implanted, wherein the bioprotective layer comprises a silicone elastomer and a poly(ethylene oxide) and poly(propylene oxide) co-polymer. One embodiment further includes a diffusion resistance layer positioned between the enzyme layer and the bioprotective layer. In one embodiment, the diffusion resistance layer also comprises the silicone elastomer and the poly(ethylene oxide) and poly(propylene oxide) co-polymer. In one embodiment, the ratio of the silicone elastomer to the co-polymer is different in the diffusion resistance layer than in the bioprotective layer. One embodiment further includes a cell disruptive layer positioned between the bioprotective layer and tissue adjacent to the sensor when implanted. In one embodiment, the silicone elastomer is a dimethyl- and methylhydrogen-siloxane copolymer. In one embodiment, the silicone elastomer comprises vinyl substituents. In one embodiment, the silicone elastomer is an elastomer produced by curing a MED-4840 mixture. In one embodiment, the copolymer comprises hydroxy substituents. In one embodiment, the co-polymer is a triblock poly(ethylene oxide)-poly(propylene oxide)-poly(ethylene oxide) polymer. In one embodiment, the co-polymer is a triblock poly(propylene oxide)-poly(ethylene oxide)-poly(propylene oxide) polymer. In one embodiment, the co-polymer is a PLURONIC® polymer. In one embodiment, the co-polymer is PLURONIC® F-127. In one embodiment, the analyte is glucose. In one embodiment, at least a portion of the co-polymer is cross-linked. In one embodiment, from about 5% w/w to about 30% w/w of the bioprotective layer is the co-polymer. In one embodiment, the enzyme layer also comprises the silicone elastomer and the co-polymer. In one embodiment, the ratio of the silicone elastomer to the co-polymer is different in the enzyme layer than in the bioprotective layer. In one embodiment, the sensor is configured to be wholly implanted. In one embodiment, the sensor is configured to be transcutaneously implanted. In one embodiment, at least a portion of the bioprotective layer is porous and adjacent to tissue when implanted.

Another embodiment disclosed herein includes an implantable analyte sensor having an enzyme layer comprising an enzyme for which the analyte is a substrate and a diffusion resistance layer comprising a silicone elastomer and a poly(ethylene oxide) and poly(propylene oxide) co-polymer, wherein the diffusion resistance layer is positioned between the enzyme layer and tissue adjacent to the sensor when implanted. One embodiment further includes a bioprotective layer positioned between the diffusion resistance layer and tissue adjacent to the sensor when implanted. In one embodiment, the silicone elastomer is a dimethyl- and methylhydrogen-siloxane copolymer. In one embodiment, the silicone elastomer comprises vinyl substituents. In one embodiment, the silicone elastomer is an elastomer produced by curing a MED-4840 mixture. In one embodiment, the copolymer comprises hydroxy substituents. In one embodiment, the co-polymer is a PLURONIC® polymer. In one embodiment, the co-polymer is PLURONIC® F-127. In one embodiment, the analyte is glucose. In one embodiment, at least a portion of the co-polymer is cross-linked. In one embodiment, from about 5% w/w to about 30% w/w of the diffusion resistance layer is the co-polymer. In one embodiment, the ratio of the silicone elastomer to co-polymer varies within the diffusion resistance layer. In one embodiment, the sensor is configured to be wholly implanted. In one embodiment, the sensor is configured to be transcutaneously implanted.

Another embodiment disclosed herein includes an implantable analyte sensor having at least one polymer membrane, wherein every polymer membrane in the sensor comprises a silicone elastomer and a poly(ethylene oxide) and poly(propylene oxide) co-polymer. In one embodiment, the silicone elastomer is a dimethyl- and methylhydrogen-siloxane copolymer. In one embodiment, the silicone elastomer comprises vinyl substituents. In one embodiment, the silicone elastomer is an elastomer produced by curing a MED-4840 mixture. In one embodiment, the copolymer comprises hydroxy substituents. In one embodiment, the co-polymer is a PLURONIC® polymer. In one embodiment, the co-polymer is PLURONIC® F-127. In one embodiment, at least a portion of the co-polymer is cross-linked. In one embodiment, from about 5% w/w to about 30% w/w of each polymer membrane is the co-polymer. In one embodiment, the sensor comprises at least two polymer membranes having a ratio of the silicone elastomer to the co-polymer that is different. In one embodiment, the sensor is configured to be wholly implanted. In one embodiment, the sensor is configured to be transcutaneously implanted.

Another embodiment disclosed herein includes a method of manufacturing a membrane for use in an analyte sensor, the method including mixing a precursor of a silicone elastomer with a poly(ethylene oxide) and poly(propylene oxide) copolymer and heating the mixture. In one embodiment, the ratio of co-polymer to silicone elastomer that is mixed is from about 1:20 w/w to about 1:4 w/w. One embodiment further includes mixing the co-polymer with a cross-linking agent. In one embodiment, the cross-linking agent is mixed with the co-polymer prior to mixing the co-polymer with the silicone elastomer precursor. In one embodiment, the cross-linking agent is selected from the group consisting of one or more of ethylene glycol diglycidyl ether and poly(ethylene glycol) diglycidyl ether. In one embodiment, the cross-linking agent comprises dicumyl peroxide. In one embodiment, the ratio of cross-linking agent to co-polymer is from about 10 cross-linking agent molecules per co-polymer molecule to about 30 cross-linking agent molecules per co-polymer molecule. In one embodiment, the amount of cross-linking agent added relative to the silicone elastomer and co-polymer is from about 0.5% to about 15% w/w. One embodiment further includes, after the mixing step but before the heating step, drawing the mixture into a thin film. One embodiment further includes, after the drawing step but before the heating step, placing a piece of porous silicon on the thin film.

DETAILED DESCRIPTION OF THE PREFERRED EMBODIMENT

Figure 1:
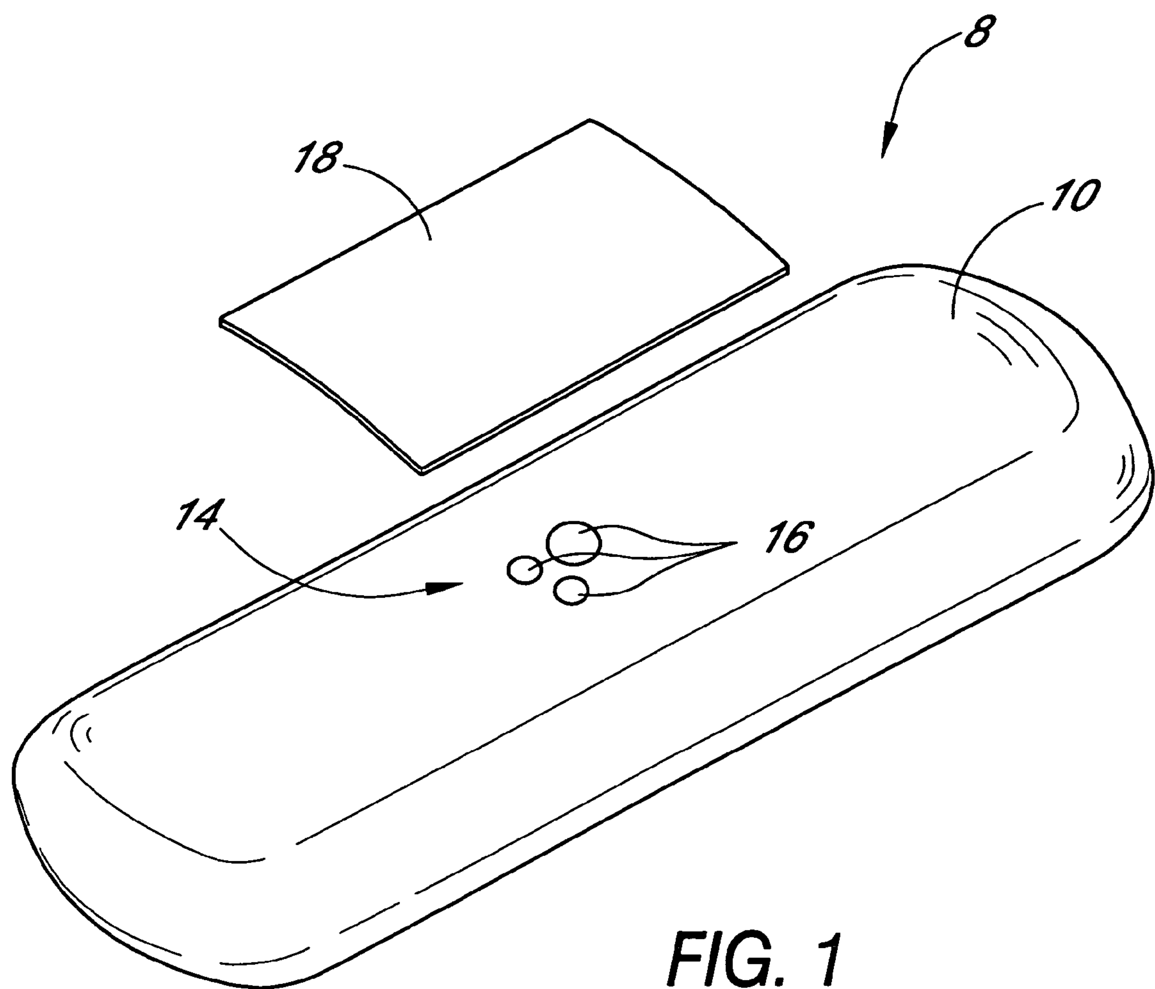
FIG. 1 is an exploded perspective view of an implantable glucose sensor in one exemplary embodiment.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the preferred embodiments, a number of terms are defined below.

The term “analyte” as used herein is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococus granulosus, Entamobea histolytica*, enterovirus, *Giardia duodenalisa, Helicobacter pylori*, hepatitis B virus, herpes virus, HIV-1, IgE (atopic disease), influenza virus, *Leishmania donovani, leptospira*, measles/mumps/rubella, *Mycobacterium leprae, Mycoplasma pneumoniae*, Myoglobin, *Onchocerca volvulus*, parainfluenza virus, Plasmodium falciparum, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The terms "operable connection," "operably connected," and "operably linked" as used herein are broad terms, and are to be given their ordinary and customary meaning to a person of ordinary skill in the art (and are not to be limited to a special or customized meaning), and refer without limitation to one or more components linked to another component(s) in a manner that allows transmission of signals between the components. For example, one or more electrodes can be used to detect the amount of analyte in a sample and convert that information into a signal; the signal can then be transmitted to a circuit. In this case, the electrode is "operably linked" to the electronic circuitry.

The term "host" as used herein is a broad term, and is to be given its ordinary and customary meaning to a person of ordinary skill in the art (and is not to be limited to a special or customized meaning), and refers without limitation to animals and plants, for example humans.

The terms "electrochemically reactive surface" and "electroactive surface" as used herein are broad terms, and are to be given their ordinary and customary meaning to a person of ordinary skill in the art (and are not to be limited to a special or customized meaning), and refer without limitation to the surface of an electrode where an electrochemical reaction takes place. As one example, a working electrode measures hydrogen peroxide produced by the enzyme catalyzed reaction of the analyte being detected reacts creating an electric current (for example, detection of glucose analyte utilizing glucose oxidase produces $H_2O_2$ as a by product, $H_2O_2$ reacts with the surface of the working electrode producing two protons ($2H_+$), two electrons ($2e^-$) and one molecule of oxygen ($O_2$) which produces the electronic current being detected). In the case of the counter electrode, a reducible species, for example, $O_2$ is reduced at the electrode surface in order to balance the current being generated by the working electrode.

The term "sensing region" as used herein is a broad term, and is to be given its ordinary and customary meaning to a person of ordinary skill in the art (and is not to be limited to a special or customized meaning), and refers without limitation to the region of a monitoring device responsible for the detection of a particular analyte. The sensing region generally comprises a non-conductive body, a working electrode, a reference electrode, and/or a counter electrode (optional) passing through and secured within the body forming electrochemically reactive surfaces on the body, an electronic connective means at another location on the body, and a multi-domain membrane affixed to the body and covering the electrochemically reactive surface.

The terms "raw data stream" and "data stream" as used herein are broad terms, and are to be given their ordinary and customary meaning to a person of ordinary skill in the art (and are not to be limited to a special or customized meaning), and refer without limitation to an analog or digital signal directly related to the measured glucose concentration from the glucose sensor. In one example, the raw data stream is digital data in "counts" converted by an A/D converter from an analog signal (for example, voltage or amps) representative of a glucose concentration. The terms broadly encompass a plurality of time spaced data points from a substantially continuous glucose sensor, which comprises individual measurements taken at time intervals ranging from fractions of a second up to, for example, 1, 2, or 5 minutes or longer.

The term "counts" as used herein is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from the working electrode. In another example, counter electrode voltage measured in counts is directly related to a voltage.

The term "electrical potential" as used herein is a broad term, and is to be given its ordinary and customary meaning to a person of ordinary skill in the art (and is not to be limited to a special or customized meaning), and refers without limitation to the electrical potential difference between two points in a circuit which is the cause of the flow of a current.

The term "ischemia" as used herein is a broad term, and is to be given its ordinary and customary meaning to a person of ordinary skill in the art (and is not to be limited to a special or customized meaning), and refers without limitation to local and temporary deficiency of blood supply due to obstruction of circulation to a part (for example, sensor). Ischemia can be caused by mechanical obstruction (for example, arterial narrowing or disruption) of the blood supply, for example.

The term "system noise" as used herein is a broad term, and is to be given its ordinary and customary meaning to a person of ordinary skill in the art (and is not to be limited to a special or customized meaning), and refers without limitation to unwanted electronic or diffusion-related noise which can include Gaussian, motion-related, flicker, kinetic, or other white noise, for example.

The terms "signal artifacts" and "transient non-glucose related signal artifacts," as used herein are broad terms, and are to be given their ordinary and customary meaning to a person of ordinary skill in the art (and are not to be limited to a special or customized meaning), and refer without limitation to signal noise that is caused by substantially non-glucose reaction rate-limiting phenomena, such as ischemia, pH changes, temperature changes, pressure, and stress, for example. Signal artifacts, as described herein, are typically transient and are characterized by higher amplitude than system noise.

The terms "low noise" as used herein is a broad term, and is to be given its ordinary and customary meaning to a person of ordinary skill in the art (and is not to be limited to a special or customized meaning), and refers without limitation to noise that substantially decreases signal amplitude.

The terms "high noise" and "high spikes" as used herein are broad terms, and are to be given their ordinary and customary meaning to a person of ordinary skill in the art (and are not to be limited to a special or customized meaning), and refer without limitation to noise that substantially increases signal amplitude.

The term "silicone composition" as used herein is a broad term, and is to be given its ordinary and customary meaning to a person of ordinary skill in the art (and is not to be limited to a special or customized meaning), and refers without limitation to a composition of matter that comprises polymers having at least silicon and oxygen atoms in the backbone.

The phrase "distal to" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. For example, some embodiments of a device include a membrane system having a cell disruptive domain and a cell impermeable domain. If the sensor is deemed to be the point of reference and the cell disruptive domain is positioned farther from the sensor, then that domain is distal to the sensor.

The phrase "proximal to" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. For example, some embodiments of a device include a membrane system having a cell disruptive domain and a cell impermeable domain. If the sensor is deemed to be the point of reference and the cell impermeable domain is positioned nearer to the sensor, then that domain is proximal to the sensor.

The terms "interferants" and "interfering species" as used herein are broad terms, and are to be given their ordinary and customary meaning to a person of ordinary skill in the art (and are not to be limited to a special or customized meaning), and refer without limitation to effects and/or species that interfere with the measurement of an analyte of interest in a sensor to produce a signal that does not accurately represent the analyte measurement. In an exemplary electrochemical sensor, interfering species can include compounds with an oxidation potential that overlaps with that of the analyte to be measured.

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade).

Overview

Membrane systems of the preferred embodiments are suitable for use with implantable devices in contact with a biological fluid. For example, the membrane systems can be utilized with implantable devices such as devices for monitoring and determining analyte levels in a biological fluid, for example, glucose levels for individuals having diabetes. In some embodiments, the analyte-measuring device is a continuous device. Alternatively, the device can analyze a plurality of intermittent biological samples. The analyte-measuring device can use any method of analyte-measurement, including enzymatic, chemical, physical, electrochemical, spectrophotometric, polarimetric, calorimetric, radiometric, or the like.

Although some of the description that follows is directed at glucose-measuring devices, including the described membrane systems and methods for their use, these membrane systems are not limited to use in devices that measure or monitor glucose. These membrane systems are suitable for use in a variety of devices, including, for example, those that detect and quantify other analytes present in biological fluids (including, but not limited to, cholesterol, amino acids, alcohol, galactose, and lactate), cell transplantation devices (see, for example, U.S. Pat. Nos. 6,015,572, 5,964,745, and 6,083,523), drug delivery devices (see, for example, U.S. Pat. Nos. 5,458,631, 5,820,589, and 5,972,369), and the like. Preferably, implantable devices that include the membrane systems of the preferred embodiments are implanted in soft tissue, for example, abdominal, subcutaneous, and peritoneal tissues, the brain, the intramedullary space, and other suitable organs or body tissues.

In addition to the glucose-measuring device described below, the membrane systems of the preferred embodiments can be employed with a variety of known glucose measuring-devices. In some embodiments, the electrode system can be used with any of a variety of known in vivo analyte sensors or monitors, such as U.S. Pat. No. 6,001,067 to Shults et al.; U.S. Pat. No. 6,702,857 to Brauker et al.; U.S. Pat. No. 6,212,416 to Ward et al.; U.S. Pat. No. 6,119,028 to Schulman et al.; U.S. Pat. No. 6,400,974 to Lesho; U.S. Pat. No. 6,595,919 to Berner et al.; U.S. Pat. No. 6,141,573 to Kurnik et al.; U.S. Pat. No. 6,122,536 to Sun et al.; European Patent Application EP 1153571 to Varall et al.; U.S. Pat. No. 6,512,939 to Colvin et al.; U.S. Pat. No. 5,605,152 to Slate et al.; U.S. Pat. No. 4,431,004 to Bessman et al.; U.S. Pat. No. 4,703,756 to Gough et al.; U.S. Pat. No. 6,514,718 to Heller et al.; U.S. Pat. No. 5,985,129 to Gough et al.; WO Patent Application Publication No. 04/021877 to Caduff; U.S. Pat. No. 5,494,562 to Maley et al.; U.S. Pat. No. 6,120,676 to Heller et al.; and U.S. Pat. No. 6,542,765 to Guy et al., each of which are incorporated in there entirety herein by reference. In general, it is understood that the disclosed embodiments are applicable to a variety of continuous glucose measuring device configurations.

FIG. 1 is an exploded perspective view of one exemplary embodiment comprising an implantable glucose sensor 10 that utilizes amperometric electrochemical sensor technology to measure glucose. In this exemplary embodiment, a body 12 with a sensing region 14 includes an electrode system 16 and sensor electronics, which are described in more detail with reference to FIG. 2.

In this embodiment, the electrode system 16 is operably connected to the sensor electronics (FIG. 2) and includes electroactive surfaces, which are covered by a membrane system 18. The membrane system 18 is disposed over the electroactive surfaces of the electrode system 16 and provides one or more of the following functions: 1) supporting tissue ingrowth (cell disruptive domain); 2) protection of the exposed electrode surface from the biological environment (cell impermeable domain); 3) diffusion resistance (limitation) of the analyte (resistance domain); 4) a catalyst for enabling an enzymatic reaction (enzyme domain); 5) limitation or blocking of interfering species (interference domain); and/or 6) hydrophilicity at the electrochemically reactive surfaces of the sensor interface (electrolyte domain), for example, as described in co-pending U.S. patent application Ser. No. 10/838,912, filed May 3, 2004, published in Publication No. 20050245799, and entitled "IMPLANTABLE ANALYTE SENSOR," the contents of which are hereby incorporated herein by reference in their entirety. The membrane system can be attached to the sensor body 12 by mechanical or chemical methods, for example, such as is described in the co-pending application Ser. No. 10/838,912 mentioned above.

Figure 5:
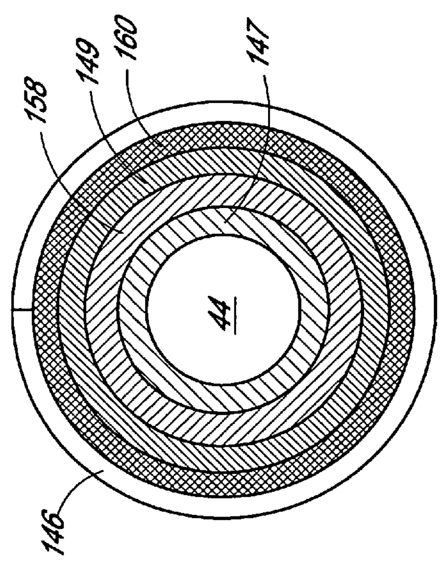
FIG. 5 is a cross-sectional view through the sensor of FIG. 3 on line C-C, showing an exposed electroactive surface of a working electrode surrounded by a membrane system.
Figure 6:
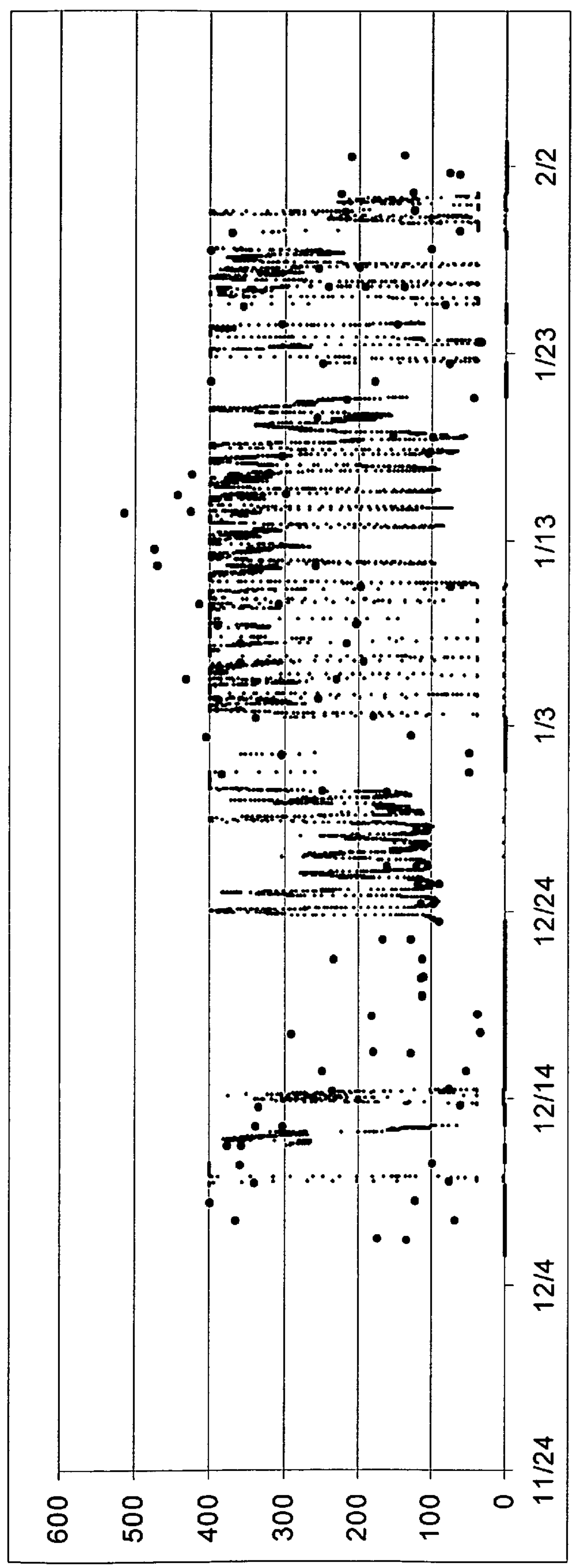
FIG. 6 is a graph depicting glucose measurements from a sensor including a silicon/hydrophilic-hydrophobic polymer blend in a diffusion resistance layer implanted in a diabetic rat model.

The membrane system 18 of the preferred embodiments, which are described in more detail below with reference to FIGS. 5 and 6, is formed at least partially from silicone materials. While not being bound by any particular theory, it is believed that silicone materials provide enhanced bio-stability when compared to other polymeric materials such as polyurethane. In addition, when a porous silicone cell disruptive layer (described in detail below) is used, silicone included in any underlying layer can promote bonding of the layer to the porous silicone cell disruptive layer. Finally, silicone has high oxygen permeability, thus promoting oxygen transport to the enzyme layer (described in detail below).

In some embodiments, the electrode system 16, which is located on or within the sensing region 14, is comprised of at least a working and a reference electrode with an insulating material disposed therebetween. In some alternative embodiments, additional electrodes can be included within the electrode system, for example, a three-electrode system (working, reference, and counter electrodes) and/or including an additional working electrode (which can be used to generate oxygen, measure an additional analyte, or can be configured as a baseline subtracting electrode, for example).

In the exemplary embodiment of FIG. 1, the electrode system includes three electrodes (working, counter, and reference electrodes), wherein the counter electrode is provided to balance the current generated by the species being measured at the working electrode. In the case of a glucose oxidase based glucose sensor, the species being measured at the working electrode is $H_2O_2$. Glucose oxidase, GOX, catalyzes the conversion of oxygen and glucose to hydrogen peroxide and gluconate according to the following reaction:

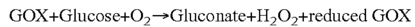

$$GOX+Glucose+O_2 \rightarrow Gluconate+H_2O_2+reduced\ GOX$$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons (2H+), two electrons (2e−), and one oxygen molecule ($O_2$). In such embodiments, because the counter electrode utilizes oxygen as an electron acceptor, the most likely reducible species for this system are oxygen or enzyme generated peroxide. There are two main pathways by which oxygen can be consumed at the counter electrode. These pathways include a four-electron pathway to produce hydroxide and a two-electron pathway to produce hydrogen peroxide. In addition to the counter electrode, oxygen is further consumed by the reduced glucose oxidase within the enzyme domain. Therefore, due to the oxygen consumption by both the enzyme and the counter electrode, there is a net consumption of oxygen within the electrode system. Theoretically, in the domain of the working electrode there is significantly less net loss of oxygen than in the region of the counter electrode. In addition, there is a close correlation between the ability of the counter electrode to maintain current balance and sensor function.

In general, in electrochemical sensors wherein an enzymatic reaction depends on oxygen as a co-reactant, depressed function or inaccuracy can be experienced in low oxygen environments, for example in vivo. Subcutaneously implanted devices are especially susceptible to transient ischemia that can compromise device function; for example, because of the enzymatic reaction required for an implantable amperometric glucose sensor, oxygen must be in excess over glucose in order for the sensor to effectively function as a glucose sensor. If glucose becomes in excess, the sensor turns into an oxygen sensitive device. In vivo, glucose concentration can vary from about one hundred times or more that of the oxygen concentration. Consequently, oxygen becomes a limiting reactant in the electrochemical reaction and when insufficient oxygen is provided to the sensor, the sensor is unable to accurately measure glucose concentration. Those skilled in the art interpret oxygen limitations resulting in depressed function or inaccuracy as a problem of availability of oxygen to the enzyme and/or counter electrode. Oxygen limitations can also be seen during periods of transient ischemia that occur, for example, under certain postures or when the region around the implanted sensor is compressed so that blood is forced out of the capillaries. Such ischemic periods observed in implanted sensors can last for many minutes or even an hour or longer.

Figure 2:
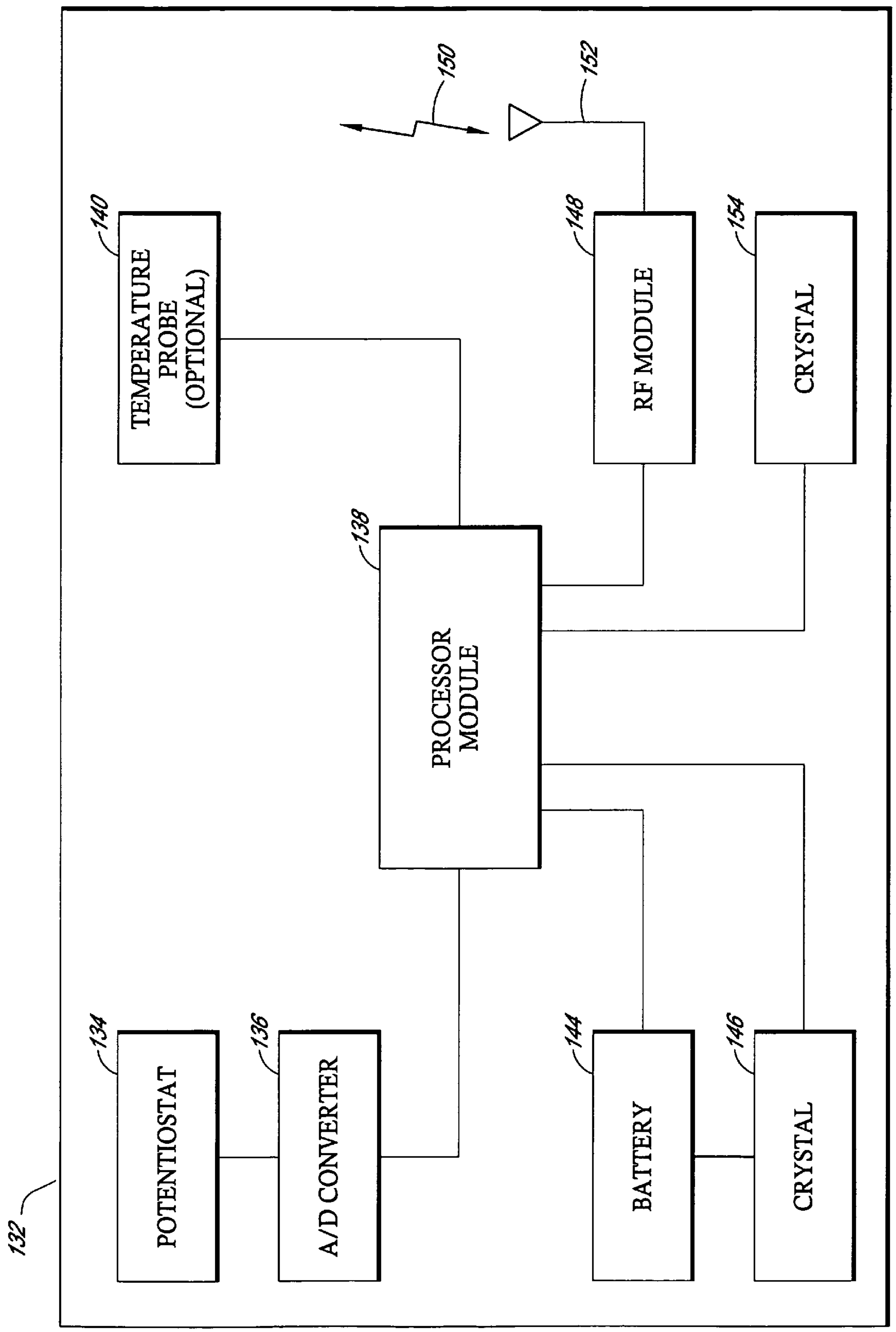
FIG. 2 is a block diagram that illustrates the sensor electronics in one embodiment; however a variety of sensor electronics configurations can be implemented with the preferred embodiments.

FIG. 2 is a block diagram that illustrates the sensor electronics in one embodiment. In this embodiment, a potentiostat 134 is shown, which is operably connected to an electrode system (such as described above) and provides a voltage to the electrodes, which biases the sensor to enable measurement of an current signal indicative of the analyte concentration in the host (also referred to as the analog portion). In some embodiments, the potentiostat includes a resistor (not shown) that translates the current into voltage. In some alternative embodiments, a current to frequency converter is provided that is configured to continuously integrate the measured current, for example, using a charge counting device.

An A/D converter 136 digitizes the analog signal into a digital signal, also referred to as "counts" for processing. Accordingly, the resulting raw data stream in counts, also referred to as raw sensor data, is directly related to the current measured by the potentiostat 134.

A processor module 138 includes the central control unit that controls the processing of the sensor electronics 132. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing and/or replacement of signal artifacts such as is described in U.S. Publication No. US-2005-0043598-A1). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, or the like.

In some embodiments, the processor module comprises a digital filter, for example, an infinite impulse response (IIR) or finite impulse response (FIR) filter, configured to smooth the raw data stream from the A/D converter. Generally, digital filters are programmed to filter data sampled at a predetermined time interval (also referred to as a sample rate). In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter as described above, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter. In preferred embodiments, the processor module is configured with a programmable acquisition time, namely, the predetermined time interval for requesting the digital value from the A/D converter is programmable by a user within the digital circuitry of the processor module. An acquisition time of from about 2 seconds to about 512 seconds is preferred; however any acquisition time can be programmed into the processor module. A programmable acquisition time is advantageous in optimizing noise filtration, time lag, and processing/battery power.

Preferably, the processor module is configured to build the data packet for transmission to an outside source, for example, an RF transmission to a receiver as described in more detail below. Generally, the data packet comprises a plurality of bits that can include a preamble, a unique identifier identifying the electronics unit, the receiver, or both, (e.g., sensor ID code), data (e.g., raw data, filtered data, and/or an integrated value) and/or error detection or correction. Preferably, the data (transmission) packet has a length of from about 8 bits to about 128 bits, preferably about 48 bits; however, larger or smaller packets can be desirable in certain embodiments. The processor module can be configured to transmit any combination of raw and/or filtered data. In one exemplary embodiment, the transmission packet contains a fixed preamble, a unique ID of the electronics unit, a single five-minute average (e.g., integrated) sensor data value, and a cyclic redundancy code (CRC).

In some embodiments, the processor module further comprises a transmitter portion that determines the transmission interval of the sensor data to a receiver, or the like. In some embodiments, the transmitter portion, which determines the interval of transmission, is configured to be programmable. In one such embodiment, a coefficient can be chosen (e.g., a number of from about 1 to about 100, or more), wherein the coefficient is multiplied by the acquisition time (or sampling rate), such as described above, to define the transmission interval of the data packet. Thus, in some embodiments, the transmission interval is programmable from about 2 seconds to about 850 minutes, more preferably from about 30 second to about 5 minutes; however, any transmission interval can be programmable or programmed into the processor module. However, a variety of alternative systems and methods for providing a programmable transmission interval can also be employed. By providing a programmable transmission interval, data transmission can be customized to meet a variety of design criteria (e.g., reduced battery consumption, timeliness of reporting sensor values, etc.)

Conventional glucose sensors measure current in the nanoAmp range. In some embodiments, the preferred embodiments are configured to measure the current flow in the picoAmp range, and in some embodiments, femtoAmps. Namely, for every unit (mg/dL) of glucose measured, at least one picoAmp of current is measured. Preferably, the analog portion of the A/D converter 136 is configured to continuously measure the current flowing at the working electrode and to convert the current measurement to digital values representative of the current. In one embodiment, the current flow is measured by a charge counting device (e.g., a capacitor). Preferably, a charge counting device provides a value (e.g., digital value) representative of the current flow integrated over time (e.g., integrated value). In some embodiments, the value is integrated over a few seconds, a few minutes, or longer. In one exemplary embodiment, the value is integrated over 5 minutes; however, other integration periods can be chosen. Thus, a signal is provided, whereby a high sensitivity maximizes the signal received by a minimal amount of measured hydrogen peroxide (e.g., minimal glucose requirements without sacrificing accuracy even in low glucose ranges), reducing the sensitivity to oxygen limitations in vivo (e.g., in oxygen-dependent glucose sensors).

In some embodiments, the electronics unit is programmed with a specific ID, which is programmed (automatically or by the user) into a receiver to establish a secure wireless communication link between the electronics unit and the receiver.

Preferably, the transmission packet is Manchester encoded; however, a variety of known encoding techniques can also be employed.

A battery 154 is operably connected to the sensor electronics 132 and provides the power for the sensor. In one embodiment, the battery is a lithium manganese dioxide battery; however, any appropriately sized and powered battery can be used (for example, AAA, nickel-cadmium, zinc-carbon, alkaline, lithium, nickel-metal hydride, lithium-ion, zinc-air, zinc-mercury oxide, silver-zinc, and/or hermetically-sealed). In some embodiments, the battery is rechargeable, and/or a plurality of batteries can be used to power the system. The sensor can be transcutaneously powered via an inductive coupling, for example. In some embodiments, a quartz crystal 96 is operably connected to the processor 138 and maintains system time for the computer system as a whole, for example for the programmable acquisition time within the processor module.

Optional temperature probe 140 is shown, wherein the temperature probe is located on the electronics assembly or the glucose sensor itself. The temperature probe can be used to measure ambient temperature in the vicinity of the glucose sensor. This temperature measurement can be used to add temperature compensation to the calculated glucose value.

An RF module 158 is operably connected to the processor 138 and transmits the sensor data from the sensor to a receiver within a wireless transmission 160 via antenna 152. In some embodiments, a second quartz crystal 154 provides the time base for the RF carrier frequency used for data transmissions from the RF transceiver. In some alternative embodiments, however, other mechanisms, such as optical, infrared radiation (IR), ultrasonic, or the like, can be used to transmit and/or receive data.

In the RF telemetry module of the preferred embodiments, the hardware and software are designed for low power requirements to increase the longevity of the device (for example, to enable a life of from about 3 to about 24 months, or more) with maximum RF transmittance from the in vivo environment to the ex vivo environment for wholly implantable sensors (for example, a distance of from about one to ten meters or more). Preferably, a high frequency carrier signal of from about 402 MHz to about 433 MHz is employed in order to maintain lower power requirements. In some embodiments, the RF module employs a one-way RF communication link to provide a simplified ultra low power data transmission and receiving scheme. The RF transmission can be OOK or FSK modulated, preferably with a radiated transmission power (EIRP) fixed at a single power level of typically less than about 100 microwatts, preferably less than about 75 microwatts, more preferably less than about 50 microwatts, and most preferably less than about 25 microwatts.

Additionally, in wholly implantable devices, the carrier frequency may be adapted for physiological attenuation levels, which is accomplished by tuning the RF module in a simulated in vivo environment to ensure RF functionality after implantation; accordingly, the preferred glucose sensor can sustain sensor function for 3 months, 6 months, 12 months, or 24 months or more.

The above description of sensor electronics associated with the electronics unit is applicable to a variety of continuous analyte sensors, such as non-invasive, minimally invasive, and/or invasive (e.g., transcutaneous and wholly implantable) sensors. For example, the sensor electronics and data processing as well as the receiver electronics and data processing described below can be incorporated into the wholly implantable glucose sensor disclosed in U.S. Publication No. US-2005-0245799-A1 and U.S. patent application Ser. No. 10/885,476 filed Jul. 6, 2004 and entitled, "SYSTEMS AND METHODS FOR MANUFACTURE OF AN ANALYTE-MEASURING DEVICE INCLUDING A MEMBRANE SYSTEM."

Figure 3:
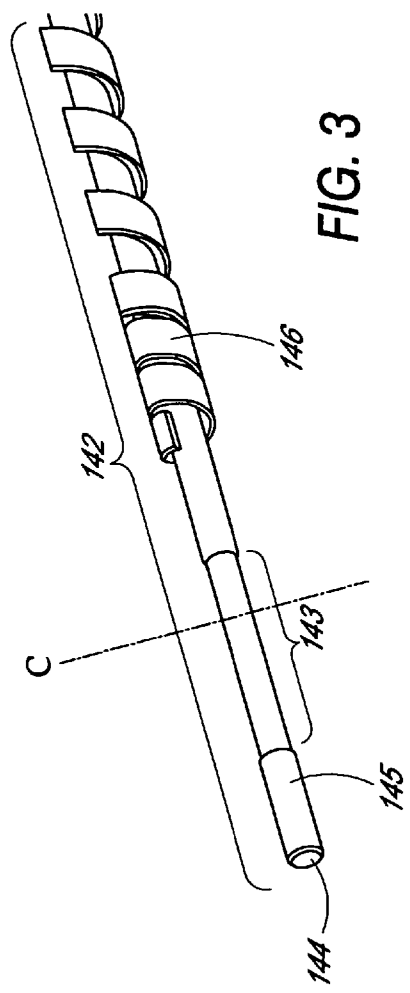
FIG. 3 is a perspective view of a transcutaneous wire analyte sensor system.

In one alternative embodiment, rather than the sensor being wholly implanted, a transcutaneous wire sensor is utilized. For example, one such suitable wire sensor 142 is depicted in FIG. 3. This sensor comprises a platinum wire working electrode 144 with insulating coating 145 (e.g., parylene). A silver or silver/silver chloride reference electrode wire 146 is helically wound around the insulating coating 145. A portion of the insulating coating 145 is removed to create an exposed electroactive window 143 around which a membrane as described herein can be disposed. Further details regarding such wire sensors may be found in U.S. application Ser. No. 11/157,746, filed Jun. 21, 2005 and entitled "TRANSCUTANEOUS ANALYTE SENSOR," which is incorporated herein by reference in its entirety.

Membrane Systems of the Preferred Embodiments

As described below with reference to FIG. 4, the membrane system 18 can include two or more layers that cover an implantable device, for example, an implantable glucose sensor. Similarly, as described below with reference to FIG. 5, two or more layers of the membrane system may be disposed on a transcutaneous wire sensor. In the example of an implantable enzyme-based electrochemical glucose sensor, the membrane prevents direct contact of the biological fluid sample with the electrodes, while controlling the permeability of selected substances (for example, oxygen and glucose) present in the biological fluid through the membrane for reaction in an enzyme rich domain with subsequent electrochemical reaction of formed products at the electrodes.

The membrane systems of preferred embodiments are constructed of one or more membrane layers. Each distinct layer can comprise the same or different materials. Furthermore, each layer can be homogenous or alternatively may comprise different domains or gradients where the composition varies.

Figure 4:
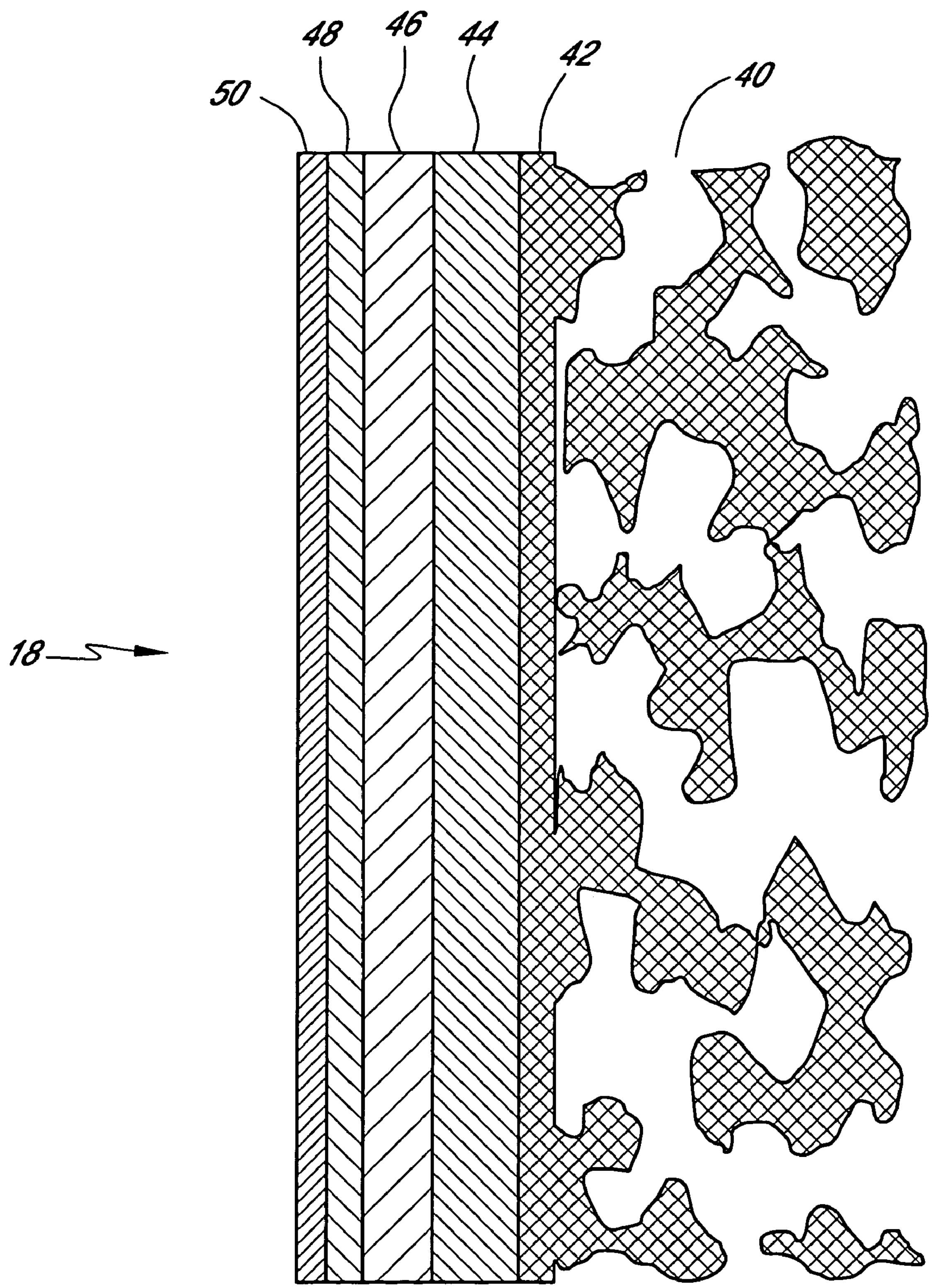
FIG. 4 is a schematic illustration of a membrane system of the device of FIG. 1.

FIG. 4 is an illustration of a membrane system in one preferred embodiment. The membrane system 18 can be used with a glucose sensor such, as is described above with reference to FIG. 1. In this embodiment, the membrane system 18 includes a cell disruptive layer 40 most distal of all domains from the electrochemically reactive surfaces, a bioprotective layer 42 less distal from the electrochemically reactive surfaces than the cell disruptive layer, a diffusion resistance layer 44 less distal from the electrochemically reactive surfaces than the bioprotective layer, an enzyme layer 46 less distal from the electrochemically reactive surfaces than the diffusion resistance layer, an interference layer 48 less distal from the electrochemically reactive surfaces than the enzyme layer, and an electrode layer 50 adjacent to the electrochemically reactive surfaces. However, it is understood that the membrane system can be modified for use in other devices, by including only two or more of the layers, or additional layers not recited above.

FIG. 5 is an illustration of a membrane system in one preferred embodiment of a transcutaneous wire sensor. FIG. 5 is a cross-sectional view through the sensor of FIG. 3 on line C-C. In this embodiment, the membrane system includes an electrode layer 147, an interference layer 158, an enzyme layer 149, and a diffusion resistance layer 160 wrapped around the platinum wire working electrode 44. In some embodiments, this membrane system also includes a cell impermeable layer as described below. In some embodiments, the transcutaneous wire sensor is configured for short-term implantation (e.g., 1-30 days). Accordingly, in these embodiments, the cell disruptive layer may not be required because a foreign body capsule does not form in the short duration of implantation.

In some embodiments, the membrane systems for use in implantable sensors is formed as a physically continuous membrane, namely, a membrane having substantially uniform physical structural characteristics from one side of the membrane to the other. However, the membrane can have chemically heterogeneous domains, for example, domains resulting from the use of block copolymers (for example, polymers in which different blocks of identical monomer units alternate with each other), but can be defined as homogeneous overall in that each of the above-described layers functions by the preferential diffusion of some substance through the homogeneous membrane.

Some layers of the membrane systems 18 of the preferred embodiments include materials with high oxygen solubility. In some embodiments, the membrane systems 18 with high oxygen solubility simultaneously permit efficient transport of aqueous solutions of the analyte.

In one embodiment, one or more layer(s) is/are formed from a composition that, in addition to providing high oxygen solubility, allows for the transport of glucose or other such water-soluble molecules (for example, drugs). In one embodiment, these layers comprise a blend of a silicone polymer with a hydrophilic polymer. By "hydrophilic polymer," it is meant that the polymer has a substantially hydrophilic domain in which aqueous substances can easily dissolve. In one embodiment, the hydrophilic polymer has a molecular weight of at least about 1000 g/mol, 5,000 g/mol, 8,000 g/mol, 10,000 g/mol, or 15,000 g/mol. In one embodiment, the hydrophilic polymer comprises both a hydrophilic domain and a partially hydrophobic domain (e.g., a copolymer). The hydrophobic domain(s) facilitate the blending of the hydrophilic polymer with the hydrophobic silicone polymer. In one embodiment, the hydrophobic domain is itself a polymer (i.e., a polymeric hydrophobic domain). For example, in one embodiment, the hydrophobic domain is not a simple molecular head group but is rather polymeric. In various embodiments, the molecular weight of any covalently continuous hydrophobic domain within the hydrophilic polymer is at least about 500 g/mol, 700 g/mol, 1000 g/mol, 2000 g/mol, 5000 g/mol, or 8,000 g/mol. In various embodiments, the molecular weight of any covalently continuous hydrophilic domain within the hydrophilic polymer is at least about 500 g/mol, 700 g/mol, 1000 g/mol, 2000 g/mol, 5000 g/mol, or 8,000 g/mol.

In various embodiments, the ratio of the silicone polymer to hydrophilic polymer in a particular layer is selected to provide an amount of oxygen and water-soluble molecule solubility such that oxygen and water-soluble molecule transport through the layer is optimized according to the desired function of that particular layer. Furthermore, in some embodiments, the ratio of silicone polymer to hydrophilic polymer as well as the polymeric compositions are selected such that a layer constructed from the material has interference characteristics that inhibit transport of one or more interfering species through the layer. Some known interfering species for a glucose sensor include, but are not limited to, acetaminophen, ascorbic acid, bilirubin, cholesterol, creatinine, dopamine, ephedrine, ibuprofen, L-dopa, methyl dopa, salicylate, tetracycline, tolazamide, tolbutamide, triglycerides, and uric acid. Accordingly, in some embodiments, a silicone polymer/hydrophilic polymer layer as disclosed herein is less permeable to one or more of these interfering species than to the analyte, e.g., glucose.

In some embodiments, silicone polymer/hydrophilic polymer blends are used in multiple layers of a membrane. In some of these embodiments, the ratio of silicone polymer to hydrophilic polymer in the layers incorporating the blends varies according to the desired functionality of each layer. The relative amounts of silicone polymer and hydrophilic polymer described below are based on the respective amounts found in the cured polymeric blend. Upon introduction into an aqueous environment, some of the polymeric components may leach out, thereby changing the relative amounts of silicone polymer and hydrophilic polymer. For example, significant amounts of the portions of the hydrophilic polymer that are not cross-linked may leach out.

In some embodiments, the amount of any cross-linking between the silicone polymer and the hydrophilic polymer is substantially limited. In various embodiments, at least about 75%, 85%, 95%, or 99% of the silicone polymer is not covalently linked to the hydrophilic polymer. In some embodiments, the silicone polymer and the hydrophilic polymer do not cross link at all unless a cross-linking agent is used (e.g., such as described below). Similarly, in some embodiments, the amount of any entanglement (e.g., blending on a molecular level) between the silicone polymer and the hydrophilic polymer is substantially limited. In one embodiment, the silicone polymer and hydrophilic polymers form microdomains. For example, in one embodiment, the silicone polymer forms micellar structures surrounded by a network of hydrophilic polymer.

The silicone polymer for use in the silicone/hydrophilic polymer blend may be any suitable silicone polymer. In some embodiments, the silicone polymer is a liquid silicone rubber that may be vulcanized using a metal- (e.g., platinum), peroxide-, heat-, ultraviolet-, or other radiation-catalyzed process. In some embodiments, the silicone polymer is a dimethyl- and methylhydrogen-siloxane copolymer. In some embodiments, the copolymer has vinyl substituents. In some embodiments, commercially available silicone polymers may be used. For example, commercially available silicone polymer precursor compositions may be used to prepare the blends, such as described below. In one embodiment, MED-4840 available from NUSIL® Technology LLC is used as a precursor to the silicone polymer used in the blend. MED-4840 consists of a 2-part silicone elastomer precursor including vinyl-functionalized dimethyl- and methylhydrogen-siloxane copolymers, amorphous silica, a platinum catalyst, a crosslinker, and an inhibitor. The two components may be mixed together and heated to initiate vulcanization, thereby forming an elastomeric solid material. Other suitable silicone polymer precursor systems include, but are not limited to, MED-2174 peroxide-cured liquid silicone rubber available from NUSIL® Technology LLC, SILASTIC® MDX4-4210 platinum-cured biomedical grade elastomer available from DOW CORNING®, and Implant Grade Liquid Silicone Polymer (durometers 10-50) available from Applied Silicone Corporation.

The hydrophilic polymer for use in the blend may be any suitable hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers (block copolymers are discussed in U.S. Pat. Nos. 4,803,243 and 4,686,044, which are incorporated herein by reference). In one embodiment, the hydrophilic polymer is a copolymer of poly(ethylene oxide) (PEO) and poly(propylene oxide) (PPO). Suitable such polymers include, but are not limited to, PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof. In some embodiments, the copolymers may be optionally substituted with hydroxy substituents. Commercially available examples of PEO and PPO copolymers include the PLURONIC® brand of polymers available from BASF®. Some PLURONIC® polymers are triblock copolymers of poly(ethylene oxide)-poly(propylene oxide)-poly(ethylene oxide) having the general molecular structure:

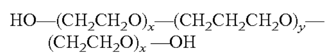

$$HO—(CH_2CH_2O)_x—(CH_2CH_2CH_2O)_y—(CH_2CH_2O)_x—OH$$

where the repeat units x and y vary among various PLURONIC® products. The poly(ethylene oxide) blocks act as a hydrophilic domain allowing the dissolution of aqueous agents in the polymer. The poly(propylene oxide) block acts as a hydrophobic domain facilitating the blending of the PLURONIC® polymer with a silicone polymer. In one embodiment, PLURONIC® F-127 is used having x of approximately 100 and y of approximately 65. The molecular weight of PLURONIC® F-127 is approximately 12,600 g/mol as reported by the manufacture. Other PLURONIC® polymers include PPO-PEO-PPO triblock copolymers (e.g., PLURONIC® R products). Other suitable commercial polymers include, but are not limited to, SYNPERONICS® products available from UNIQEMA®.

The polyether structure of PLURONIC® polymers is relatively inert. Accordingly, without being bound by any particular theory, it is believed that the PLURONIC® polymers do not substantially react with the components in MED-4840 or other silicone polymer precursors.

Those of skill in the art will appreciate that other copolymers having hydrophilic and hydrophobic domains may be used. For example, in one alternative embodiment, a triblock copolymer having the structure hydrophobic-hydrophilic-hydrophobic may be used. In another alternative embodiment, a diblock copolymer having the structure hydrophilic-hydrophobic is used.

Synthesis of Silicone/Hydrophilic Polymer Blend Layers

Layers that include a silicone polymer-hydrophilic polymer blend may be made using any of the methods of forming polymer blends known in the art. In one embodiment, a silicone polymer precursor (e.g., MED-4840) is mixed with a solution of a hydrophilic polymer (e.g., PLURONIC® F-127 dissolved in a suitable solvent such as acetone, ethyl alcohol, or 2-butanone). The mixture may then be drawn into a film or applied in a multi-layer membrane structure using any method known in the art (e.g., spraying, painting, dip coating, vapor depositing, molding, 3-D printing, lithographic techniques (e.g., photolithograph), micro- and nano-pipetting printing techniques, etc.). The mixture may then be cured under high temperature (e.g., 50-150° C.). Other suitable curing methods include ultraviolet or gamma radiation, for example. During curing, the silicone polymer precursor will vulcanize and the solvent will evaporate. In one embodiment, after the mixture is drawn into a film, another preformed layer of the membrane system is placed on the film. Curing of the film then provides bonding between the film and the other preformed layer. In one embodiment, the preformed layer is the cell disruptive layer. In one embodiment, the cell disruptive layer comprises a preformed porous silicone membrane. In other embodiments, the cell disruptive layer is also formed from a silicone polymer/hydrophilic polymer blend. In some embodiments, multiple films are applied on top of the preformed layer. Each film may posses a finite interface with adjacent films or may together form a physically continuous structure having a gradient in chemical composition.

Some amount of cross-linking agent may also be included in the mixture to induce cross-linking between hydrophilic polymer molecules. For example, when using a PLURONIC® polymer, a cross-linking system that reacts with pendant or terminal hydroxy groups or methylene, ethylene, or propylene hydrogen atoms may be used to induce cross linking. Non-limiting examples of suitable cross-linking agents include ethylene glycol diglycidyl ether (EGDE), poly (ethylene glycol) diglycidyl ether (PEGDE), or dicumyl peroxide (DCP). While not being bound by any particular theory, at low concentrations, these cross-linking agents are believed to react primarily with the PLURONIC® polymer with some amount possibly inducing cross-linking in the silicone polymer or between the PLURONIC® polymer and the silicone polymer. In one embodiment, enough cross-linking agent is added such that the ratio of cross-linking agent molecules to hydrophilic polymer molecules added when synthesizing the blend is about 10 to about 30 (e.g., about 15 to about 20). In one embodiment, from about 0.5% to about 15% w/w of cross-linking agent is added relative to the total dry weights of cross-linking agent, silicone polymer, and hydrophilic polymer added when blending the ingredients (in one example, about 1% to about 10%). In one embodiment, from about 5% to about 30% of the dry ingredient weight is the PLURONIC® polymer. During the curing process, substantially all of the cross-linking agent is believed to react, leaving substantially no detectable unreacted cross-linking agent in the final film.

In some embodiments, other agents may be added to the mixture to facilitate formation of the blend. For example, a small amount of butylhydroxy toluene (BHT) (e.g., about 0.01% w/w) or other suitable antioxidant may be mixed with a PLURONIC® to stabilize it.

In some alternative embodiments, precursors of both the silicone polymer and hydrophilic polymer may be mixed prior to curing such that polymerization of both the silicone polymer and the hydrophilic polymer occur during curing. In another embodiment, already polymerized silicone polymer is mixed with a hydrophilic polymer such that no significant polymerization occurs during curing.

Cell Disruptive Domain

The cell disruptive layer 40 is positioned most distal to the implantable device and is designed to support tissue ingrowth, to disrupt contractile forces typically found in a foreign body capsule, to encourage vascularity within the membrane, and/or to disrupt the formation of a barrier cell layer. In one embodiment, the cell disruptive layer 40 has an open-celled configuration with interconnected cavities and solid portions, wherein the distribution of the solid portion and cavities of the cell disruptive layer includes a substantially co-continuous solid domain and includes more than one cavity in three dimensions substantially throughout the entirety of the first domain. Cells can enter into the cavities; however they cannot travel through or wholly exist within the solid portions. The cavities allow most substances to pass through, including, for example, cells, and molecules. U.S. Pat. No. 6,702,857, filed Jul. 27, 2001, and entitled "MEMBRANE FOR USE WITH IMPLANTABLE DEVICES" and U.S. patent application Ser. No. 10/647,065, filed Aug. 22, 2003, published in U.S. Publication No. 2005/0112169 A1 and entitled, "POROUS MEMBRANES FOR USE WITH IMPLANTABLE DEVICES" describe membranes having a cell disruptive domain and are both incorporated herein by reference in their entirety.

The cell disruptive layer 40 is preferably formed from high oxygen soluble materials such as polymers formed from silicone, fluorocarbons, perfluorocarbons, or the like. In these embodiments, transport of water-soluble agents such as an aqueous analyte occurs primarily through the pores and cavities of the layer. In some embodiments, the cell disruptive domain is formed from polyethylene-co-tetrafluoroethylene, polyolefin, polyester, polycarbonate, biostable polytetrafluoroethylene, homopolymers, copolymers, terpolymers of polytetrafluoroethylene, polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones or block copolymers thereof including, for example, di-block, tri-block, alternating, random and graft copolymers. In other embodiments, the cell disruptive layer is formed from a silicone composition with a non-silicon containing hydrophile such as such as polyethylene glycol, propylene glycol, pyrrolidone, esters, amides, or carbonates covalently incorporated or grafted therein such that water-soluble agents can also be transported through polymeric matrix of the cell disruptive layer 40. Such compositions are described for example in U.S. application Ser. No. 10/695,636, filed Oct. 28, 2003, published in Publication No. 2005/0090607 and entitled "SILICONE COMPOSITION FOR BIOCOMPATIBLE MEMBRANE," which is incorporated herein by reference in its entirety. In still other embodiments, the cell disruptive layer is formed from a monomer, polymer, copolymer, or blend including one or more of: lactic acid, glycolic acid, anhydrides, phospazenes, vinyl alcohol, ethylene vinyl alcohol, acetates, ε-caprolactone, β-hydroxybutyrate, γ-ethyl glutamate, DTH iminocarbonate, Bisphenol A iminocarbonate, sebacic acid, hexadecanoic acid, saccharides, chitosan, hydyoxyethyl methacrylate (HEMA), ceramics, hyaluronic acid (HA), collagen, gelatin, starches, hydroxy apatite, calcium phosphates, bioglasses, amino acid sequences, proteins, glycoproteins, protein fragments, agarose, fibrin, n-butylene, isobutylene, dioxanone, nylons, vinyl chlorides, amides, ethylenes, n-butyl methacrylate (BMA), metal matrix composites (MMCs), metal oxides (e.g. aluminum), DETOSU-1,6 HD-t-CDM ortho ester, styrene, and plasma treated surfaces of any of the above.

In some embodiments, the cell disruptive layer 40 is formed from silicone polymer/hydrophilic polymer blends such as described above. Due to the open-cell configuration of the cell disruptive layer 40, the ratio of silicone polymer to hydrophilic polymer may be chosen to increase the structural integrity of the layer so that the open-cell configuration is maintained. Alternatively, the structural integrity of the cell disruptive layer can be increased by choosing a silicone polymer having properties suitable for increasing structural integrity (e.g., a silicone polymer having an increased durometer). In one embodiment, the concentration of hydrophilic polymer (e.g., PLURONIC® F-127) relative to silicone polymer (e.g., MED-4840) is from about 1% to about 30%, preferably from about 5% to about 20% in the cell disruptive layer 40.

In preferred embodiments, the thickness of the cell disruptive domain is from about 10 or less, 20, 30, 40, 50, 60, 70, 80, or 90 microns to about 1500, 2000, 2500, or 3000 or more microns. In more preferred embodiments, the thickness of the cell disruptive domain is from about 100, 150, 200 or 250 microns to about 1000, 1100, 1200, 1300, or 1400 microns. In even more preferred embodiments, the thickness of the cell disruptive domain is from about 300, 350, 400, 450, 500, or 550 microns to about 500, 550, 600, 650, 700, 750, 800, 850, or 900 microns.

The cell disruptive domain is optional and can be omitted when using an implantable device that does not prefer tissue ingrowth, for example, a short-lived device (for example, less than one day to about a week or up to about one month) or one that delivers tissue response modifiers.

Bioprotective Layer

The bioprotective layer 42 is positioned less distal to the implantable device than the cell disruptive layer, and can be resistant to cellular attachment, impermeable to cells, and/or is composed of a biostable material. When the bioprotective layer is resistant to cellular attachment (for example, attachment by inflammatory cells, such as macrophages, which are therefore kept a sufficient distance from other domains, for example, the enzyme domain), hypochlorite and other oxidizing species are short-lived chemical species in vivo, and biodegradation does not occur. Additionally, the materials preferred for forming the bioprotective layer 42 may be resistant to the effects of these oxidative species and have thus been termed biodurable. See, for example, U.S. Pat. No. 6,702,857, filed Jul. 27, 2001, and entitled "MEMBRANE FOR USE WITH IMPLANTABLE DEVICES" and U.S. patent application Ser. No. 10/647,065, filed Aug. 22, 2003, published in Publication No. 20050112169 and entitled, "POROUS MEMBRANES FOR USE WITH IMPLANTABLE DEVICES," both of which are incorporated herein by reference in their entirety.

In one embodiment, bioprotective layer 42 is formed from high oxygen soluble materials such as polymers formed from silicone, fluorocarbons, perfluorocarbons, or the like. In one embodiment, the cell impermeable domain is formed from a silicone composition with a hydrophile such as such as polyethylene glycol, propylene glycol, pyrrolidone, esters, amides, carbonates, or polypropylene glycol covalently incorporated or grafted therein. In still other embodiments, the bioprotective layer is formed from a monomer, polymer, copolymer, or blend including one or more of: lactic acid, glycolic acid, anhydrides, phospazenes, vinyl alcohol, ethylene vinyl alcohol, acetates, ε-caprolactone, β-hydroxybutyrate, γ-ethyl glutamate, DTH iminocarbonate, Bisphenol A iminocarbonate, sebacic acid, hexadecanoic acid, saccharides, chitosan, hydyoxyethyl methacrylate (HEMA), ceramics, hyaluronic acid (HA), collagen, gelatin, starches, hydroxy apatite, calcium phosphates, bioglasses, amino acid sequences, proteins, glycoproteins, protein fragments, agarose, fibrin, n-butylene, isobutylene, dioxanone, nylons, vinyl chlorides, amides, ethylenes, n-butyl methacrylate (BMA), metal matrix composites (MMCs), metal oxides (e.g. aluminum), DETOSU-1,6 HD-t-CDM ortho ester, styrene, and plasma treated surfaces of any of the above.

In one preferred embodiment, the bioprotective layer 42 is formed from silicone polymer/hydrophilic polymer blends such as described above. It is advantageous that the cell impermeable layer 42 have both high oxygen and aqueous analyte solubility so that sufficient reactants reach the enzyme layer. Accordingly, in one embodiment, the concentration of hydrophilic polymer (e.g., PLURONIC® F-127) relative to silicone polymer (e.g., MED-4840) is relatively high, e.g., from about 10% to about 30% in the bioprotective layer 42. In one embodiment, the concentration of hydrophilic polymer is from about 15% to about 25% (e.g., about 20%).

In preferred embodiments, the thickness of the bioprotective layer is from about 10 or 15 microns or less to about 125, 150, 175, 200 or 250 microns or more. In more preferred embodiments, the thickness of the bioprotective layer is from about 20, 25, 30, or 35 microns to about 60, 65, 70, 75, 80, 85, 90, 95, or 100 microns. In even more preferred embodiments, the bioprotective layer is from about 20 or 25 microns to about 50, 55, or 60 microns thick.

The cell disruptive layer 40 and bioprotective layer 42 of the membrane system can be formed together as one unitary structure. Alternatively, the cell disruptive and bioprotective layers 40, 42 of the membrane system can be formed as two layers mechanically or chemically bonded together. In one embodiment, the cell disruptive layer 40 and bioprotective layer 42 consist of a unitary structure having graduated properties. For example, the porosity of the unitary structure may vary from high porosity at the tissue side of the layer to very low or no porosity at the sensor side. In addition, the chemical properties of such a graduated structure may also vary. For example, the concentration of the hydrophilic polymer may vary throughout the structure, increasing in concentration toward the sensor side of the layer. The lower concentration on the tissue side allows for increased structural integrity to support an open-celled structure while the higher concentration on the sensor side promotes increased transport of aqueous analytes through the polymer blend.

Diffusion Resistance Layer

The diffusion resistance layer 44 or 150 is situated more proximal to the implantable device relative to the cell disruptive layer. The diffusion resistance layer controls the flux of oxygen and other analytes (for example, glucose) to the underlying enzyme domain. As described in more detail elsewhere herein, there exists a molar excess of glucose relative to the amount of oxygen in blood; that is, for every free oxygen molecule in extracellular fluid, there are typically more than 100 glucose molecules present (see Updike et al., Diabetes Care 5:207-21(1982)). However, an immobilized enzyme-based sensor employing oxygen as cofactor is supplied with oxygen in non-rate-limiting excess in order to respond linearly to changes in glucose concentration, while not responding to changes in oxygen tension. More specifically, when a glucose-monitoring reaction is oxygen-limited, linearity is not achieved above minimal concentrations of glucose. Without a semipermeable membrane situated over the enzyme domain to control the flux of glucose and oxygen, a linear response to glucose levels can be obtained only up to about 40 mg/dL. However, in a clinical setting, a linear response to glucose levels is desirable up to at least about 500 mg/dL.

The diffusion resistance layer 44 or 150 includes a semipermeable membrane that controls the flux of oxygen and glucose to the underlying enzyme layer 46 or 147, preferably rendering oxygen in non-rate-limiting excess. As a result, the upper limit of linearity of glucose measurement is extended to a much higher value than that which is achieved without the diffusion resistance layer. In one embodiment, the diffusion resistance layer 44 or 150 exhibits an oxygen-to-glucose permeability ratio of approximately 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)). In some embodiments, a lower ratio of oxygen-to-glucose can be sufficient to provide excess oxygen by using a high oxygen soluble domain (for example, a silicone material) to enhance the supply/transport of oxygen to the enzyme membrane and/or electroactive surfaces. By enhancing the oxygen supply through the use of a silicone composition, for example, glucose concentration can be less of a limiting factor. In other words, if more oxygen is supplied to the enzyme and/or electroactive surfaces, then more glucose can also be supplied to the enzyme without creating an oxygen rate-limiting excess.

In one embodiment, the diffusion resistance layer 44 or 150 is preferably formed from high oxygen soluble materials such as polymers formed from silicone, fluorocarbons, perfluorocarbons, or the like. In one embodiment, the resistance domain is formed from a silicone composition with a hydrophile such as such as polyethylene glycol, propylene glycol, pyrrolidone, esters, amides, carbonates, or polypropylene glycol covalently incorporated or grafted therein. In some alternative embodiments, the diffusion resistance layer is formed from polyurethane, for example, a polyurethane urea/polyurethane-block-polyethylene glycol blend. In still other embodiments, the diffusion resistance layer is formed from a monomer, polymer, copolymer, or blend including one or more of: lactic acid, glycolic acid, anhydrides, phospazenes, vinyl alcohol, ethylene vinyl alcohol, acetates, ϵ-caprolactone, β-hydroxybutyrate, γ-ethyl glutamate, DTH iminocarbonate, Bisphenol A iminocarbonate, sebacic acid, hexadecanoic acid, saccharides, chitosan, hydyoxyethyl methacrylate (HEMA), ceramics, hyaluronic acid (HA), collagen, gelatin, starches, hydroxy apatite, calcium phosphates, bioglasses, amino acid sequences, proteins, glycoproteins, protein fragments, agarose, fibrin, n-butylene, isobutylene, dioxanone, nylons, vinyl chlorides, amides, ethylenes, n-butyl methacrylate (BMA), metal matrix composites (MMCs), metal oxides (e.g. aluminum), DETOSU-1,6 HD-t-CDM ortho ester, styrene, and plasma treated surfaces of any of the above.

In some preferred embodiments, the diffusion resistance layer 44 or 150 is formed from silicone polymer/hydrophilic polymer blends such as described above. In some alternative embodiments, the diffusion resistance layer 44 or 150 is formed from silicone polymer/hydrophilic polymer blends. In order to restrict the transport of an aqueous analyte such as glucose, lower concentrations of hydrophilic polymer can be employed. Accordingly, in one embodiment, the concentration of hydrophilic polymer (e.g., PLURONIC® F-127) relative to silicone polymer (e.g., MED-4840) is from about 1% to about 15% in the diffusion resistance layer 44 (e.g., from about 6% to about 10%).

In some alternative embodiments, the diffusion resistance layer includes a polyurethane membrane with both hydrophilic and hydrophobic regions to control the diffusion of glucose and oxygen to an analyte sensor, the membrane being fabricated easily and reproducibly from commercially available materials. A suitable hydrophobic polymer component is a polyurethane, or polyetherurethaneurea. Polyurethane is a polymer produced by the condensation reaction of a diisocyanate and a difunctional hydroxyl-containing material. A polyurethaneurea is a polymer produced by the condensation reaction of a diisocyanate and a difunctional amine-containing material. Preferred diisocyanates include aliphatic diisocyanates containing from about 4 to about 8 methylene units. Diisocyanates containing cycloaliphatic moieties can also be useful in the preparation of the polymer and copolymer components of the membranes of preferred embodiments. The material that forms the basis of the hydrophobic matrix of the diffusion resistance layer can be any of those known in the art as appropriate for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In one embodiment, the hydrophilic polymer component is polyethylene oxide. For example, one useful hydrophilic copolymer component is a polyurethane polymer that includes about 20% hydrophilic polyethylene oxide. The polyethylene oxide portions of the copolymer are thermodynamically driven to separate from the hydrophobic portions of the copolymer and the hydrophobic polymer component. The 20% polyethylene oxid-based soft segment portion of the copolymer used to form the final blend affects the water pick-up and subsequent glucose permeability of the membrane.

In some embodiments, the diffusion resistance layer 44 or 150 can be formed as a unitary structure with the bioprotective layer 42; that is, the inherent properties of the diffusion resistance layer 44 or 150 can provide the functionality described with reference to the bioprotective layer 42 such that the bioprotective layer 42 is incorporated as a part of diffusion resistance layer 44 or 150. In these embodiments, the combined diffusion resistance layer/bioprotective layer can be bonded to or formed as a skin on the cell disruptive layer 40. As discussed above, the diffusion resistance layer/bioprotective layer may also be part of a unitary structure with the cell disruptive layer 40 such that the outer layer of the membrane system is graduated to the interface with the enzyme layer. In another embodiment, the diffusion resistance layer/bioprotective layer may also be part of a unitary structure with the cell disruptive layer 40 including a chemical gradient with transition properties between the outer layer and the enzyme layer. In another embodiment, the diffusion resistance layer 44 or 150 is formed as a distinct layer and chemically or mechanically bonded to the cell disruptive layer 40 (if applicable) or the bioprotective layer 42 (when the resistance domain is distinct from the cell impermeable domain).

In still another embodiment, the diffusion resistance layer may be a distinct layer from the cell disruptive layer or the bioprotective layer but may nonetheless include a chemical gradient such that its diffusion resistance property transitions from one side of the layer to the other. Similarly, the cell disruptive layer and bioprotective layers may also include a chemical gradient. Where multiple such layers have chemical gradients, the chemical compositions at the interface between two layers may be identical or different.

In preferred embodiments, the thickness of the resistance domain is from about 0.05 microns or less to about 200 microns or more. In more preferred embodiments, the thickness of the resistance domain is from about 0.05, 0.1, 0.15, 0.2, 0.25, 0.3, 0.35, 0.4, 0.45, 0.5, 1, 1.5, 2, 2.5, 3, 3.5, 10, 15, 20, 25, 30, or 35 microns to about, 5, 6, 7, 8, 9, 10, 11, 12, 13, 14, 15, 16, 17, 18, 19, 19.5, 20, 30, 40, 50, 60, 70, 75, 80, 85, 90, 95, or 100 microns. In more preferred embodiments, the thickness of the resistance domain is from about 2, 2.5 or 3 microns to about 3.5, 4, 4.5, or 5 microns in the case of a transcutaneously implanted sensor or from about 20 or 25 microns to about 40 or 50 microns in the case of a wholly implanted sensor.

Enzyme Layer

An immobilized enzyme layer 46 or 149 is situated less distal from the electrochemically reactive surfaces than the diffusion resistance layer 44 or 150. In one embodiment, the immobilized enzyme layer 46 or 149 comprises glucose oxidase. In other embodiments, the immobilized enzyme layer 46 or 149 can be impregnated with other oxidases, for example, galactose oxidase, cholesterol oxidase, amino acid oxidase, alcohol oxidase, lactate oxidase, or uricase. For example, for an enzyme-based electrochemical glucose sensor to perform well, the sensor's response should neither be limited by enzyme activity nor cofactor concentration.

The enzyme layer 44 or 149 is preferably formed from high oxygen soluble materials such as polymers formed from silicone, fluorocarbons, perfluorocarbons, or the like. In one embodiment, the enzyme domain is formed from a silicone composition with a hydrophile such as such as polyethylene glycol, propylene glycol, pyrrolidone, esters, amides, carbonates, or polypropylene glycol covalently incorporated or grafted therein. In one embodiment, the enzyme layer 44 or 149 is formed from polyurethane.

In one embodiment, high oxygen solubility within the enzyme layer can be achieved by using a polymer matrix to host the enzyme within the enzyme layer that has a high solubility of oxygen. In one exemplary embodiment of fluorocarbon-based polymers, the solubility of oxygen within a perfluorocarbon-based polymer is 50-volume %. As a reference, the solubility of oxygen in water is approximately 2-volume %.

In one preferred embodiment, the enzyme layer is formed from silicone polymer/hydrophilic polymer blends such as described above. In one embodiment, the concentration of hydrophilic polymer (e.g., PLURONIC® F-127) relative to silicone polymer (e.g., MED-4840) is relatively high, e.g., from about 10% to about 30% in the bioprotective layer 42. In one embodiment, the concentration of hydrophilic polymer is from about 15% to about 25% (e.g., about 20%).

Utilization of a high oxygen solubility material for the enzyme layer is advantageous because the oxygen dissolves more readily within the layer and thereby acts as a high oxygen soluble domain optimizing oxygen availability to oxygen-utilizing sources (for example, the enzyme and/or counter electrode). When the diffusion resistance layer 44 or 149 and enzyme layer 46 or 150 both comprise a high oxygen soluble material, the chemical bond between the enzyme layer 46 or 150 and diffusion resistance layer 44 or 149 can be optimized, and the manufacturing made easy.

In some alternative embodiments, the enzyme domain is constructed of aqueous dispersions of colloidal polyurethane polymers including the enzyme.

In preferred embodiments, the thickness of the enzyme domain is from about 0.05 micron or less to about 20, 30 40, 50, 60, 70, 80, 90, or 100 microns or more. In more preferred embodiments, the thickness of the enzyme domain is between about 0.05, 0.1, 0.15, 0.2, 0.25, 0.3, 0.35, 0.4, 0.45, 0.5, 1, 1.5, 2, 2.5, 3, 4, or 5 microns and 4, 5, 6, 7, 8, 9, 10, 11, 12, 13, 14, 15, 16, 17, 18, 19, 19.5, 20, 25, or 30 microns. In even more preferred embodiments, the thickness of the enzyme domain is from about 2, 2.5, or 3 microns to about 3.5, 4, 4.5, or 5 microns in the case of a transcutaneously implanted sensor or from about 6, 7, or 8 microns to about 9, 10, 11, or 12 microns in the case of a wholly implanted sensor.

Interference Layer

The interference layer 48 or 148 is situated less distal to the implantable device than the immobilized enzyme layer. Interferants are molecules or other species that are electro-reduced or electro-oxidized at the electrochemically reactive surfaces, either directly or via an electron transfer agent, to produce a false signal (for example, urate, ascorbate, or acetaminophen). In one embodiment, the interference layer 48 or 148 prevents the penetration of one or more interferants into the electrolyte phase around the electrochemically reactive surfaces. Preferably, this type of interference layer is much less permeable to one or more of the interferants than to the analyte.

In one embodiment, the interference domain 48 or 148 can include ionic components incorporated into a polymeric matrix to reduce the permeability of the interference layer to ionic interferants having the same charge as the ionic components. In another embodiment, the interference layer 48 or 148 includes a catalyst (for example, peroxidase) for catalyzing a reaction that removes interferants. U.S. Pat. Nos. 6,413,396 and 6,565,509 disclose methods and materials for eliminating interfering species, both of which are incorporated herein by reference in their entirety; however in the preferred embodiments any suitable method or material can be employed.

In another embodiment, the interference layer 48 or 148 includes a thin membrane that is designed to limit diffusion of species, for example, those greater than 34 kD in molecular weight, for example. The interference layer permits analytes and other substances (for example, hydrogen peroxide) that are to be measured by the electrodes to pass through, while preventing passage of other substances, such as potentially interfering substances. In one embodiment, the interference layer 48 or 148 is constructed of polyurethane. In an alternative embodiment, the interference layer 48 or 148 comprises a high oxygen soluble polymer.

In one embodiment, the interference layer 48 or 148 is formed from silicone polymer/hydrophilic polymer blends such as described above. As described herein, such polymer blends can have the characteristics of limiting transport of one or more interferants therethrough. Because of this property, the use of the polymer blends in a membrane layer other than the interference layer may also confer interferant resistance properties in those layers, potentially eliminating the need for a separate interference layer. In some embodiments, these layers allow diffusion of glucose therethrough but limit diffusion of one or more interferant therethrough.

In some embodiments, the interference layer 48 or 148 is formed from one or more cellulosic derivatives. In general, cellulosic derivatives include polymers such as cellulose acetate, cellulose acetate butyrate, 2-hydroxyethyl cellulose, cellulose acetate phthalate, cellulose acetate propionate, cellulose acetate trimellitate, and the like.

In one preferred embodiment, the interference layer 48 or 148 is formed from cellulose acetate butyrate. Cellulose acetate butyrate with a molecular weight of about 10,000 daltons to about 75,000 daltons, preferably from about 15,000, 20,000, or 25,000 daltons to about 50,000, 55,000, 60,000, 65,000, or 70,000 daltons, and more preferably about 20,000 daltons is employed. In certain embodiments, however, higher or lower molecular weights can be preferred. Additionally, a casting solution or dispersion of cellulose acetate butyrate at a weight percent of about 15% to about 25%, preferably from about 15%, 16%, 17%, 18%, 19% to about 20%, 21%, 22%, 23%, 24% or 25%, and more preferably about 18% is preferred. Preferably, the casting solution includes a solvent or solvent system, for example an acetone: ethanol solvent system. Higher or lower concentrations can be preferred in certain embodiments. A plurality of layers of cellulose acetate butyrate can be advantageously combined to form the interference domain in some embodiments, for example, three layers can be employed. It can be desirable to employ a mixture of cellulose acetate butyrate components with different molecular weights in a single solution, or to deposit multiple layers of cellulose acetate butyrate from different solutions comprising cellulose acetate butyrate of different molecular weights, different concentrations, and/or different chemistries (e.g., functional groups). It can also be desirable to include additional substances in the casting solutions or dispersions, e.g., functionalizing agents, crosslinking agents, other polymeric substances, substances capable of modifying the hydrophilicity/hydrophobicity of the resulting layer, and the like.

In one alternative embodiment, the interference layer 48 or 148 is formed from cellulose acetate. Cellulose acetate with a molecular weight of about 30,000 daltons or less to about 100,000 daltons or more, preferably from about 35,000, 40,000, or 45,000 daltons to about 55,000, 60,000, 65,000, 70,000, 75,000, 80,000, 85,000, 90,000, or 95,000 daltons, and more preferably about 50,000 daltons is preferred. Additionally, a casting solution or dispersion of cellulose acetate at a weight percent of about 3% to about 10%, preferably from about 3.5%, 4.0%, 4.5%, 5.0%, 5.5%, 6.0%, or 6.5% to about 7.5%, 8.0%, 8.5%, 9.0%, or 9.5%, and more preferably about 8% is preferred. In certain embodiments, however, higher or lower molecular weights and/or cellulose acetate weight percentages can be preferred. It can be desirable to employ a mixture of cellulose acetates with molecular weights in a single solution, or to deposit multiple layers of cellulose acetate from different solutions comprising cellulose acetates of different molecular weights, different concentrations, or different chemistries (e.g., functional groups). It can also be desirable to include additional substances in the casting solutions or dispersions such as described in more detail above.

Layer(s) prepared from combinations of cellulose acetate and cellulose acetate butyrate, or combinations of layer(s) of cellulose acetate and layer(s) of cellulose acetate butyrate can also be employed to form the interference layer 48 or 148.

In some alternative embodiments, additional polymers, such as Nafion® can be used in combination with cellulosic derivatives to provide equivalent and/or enhanced function of the interference layer 48 or 148. As one example, a 5 wt % Nafion® casting solution or dispersion can be used in combination with a 8 wt % cellulose acetate casting solution or dispersion, e.g., by dip coating at least one layer of cellulose acetate and subsequently dip coating at least one layer Nafion® onto a needle-type sensor such as described with reference to the preferred embodiments. Any number of coatings or layers formed in any order may be suitable for forming the interference domain of the preferred embodiments.

In some alternative embodiments, more than one cellulosic derivative can be used to form the interference layer 48 or 148 of the preferred embodiments. In general, the formation of the interference domain on a surface utilizes a solvent or solvent system in order to solvate the cellulosic derivative (or other polymer) prior to film formation thereon. In preferred embodiments, acetone and ethanol are used as solvents for cellulose acetate; however one skilled in the art appreciates the numerous solvents that are suitable for use with cellulosic derivatives (and other polymers). Additionally, one skilled in the art appreciates that the preferred relative amounts of solvent can be dependent upon the cellulosic derivative (or other polymer) used, its molecular weight, its method of deposition, its desired thickness, and the like. However, a percent solute of from about 1% to about 25% is preferably used to form the interference domain solution so as to yield an interference layer 48 or 148 having the desired properties. The cellulosic derivative (or other polymer) used, its molecular weight, method of deposition, and desired thickness can be adjusted, depending upon one or more other of the parameters, and can be varied accordingly as is appreciated by one skilled in the art.

In some alternative embodiments, other polymer types that can be utilized as a base material for the interference layer 48 or 148 include polyurethanes, polymers having pendant ionic groups, and polymers having controlled pore size, for example. In one such alternative embodiment, the interference domain includes a thin, hydrophobic membrane that is non-swellable and restricts diffusion of low molecular weight species. The interference layer 48 or 148 is permeable to relatively low molecular weight substances, such as hydrogen peroxide, but restricts the passage of higher molecular weight substances, including glucose and ascorbic acid. Other systems and methods for reducing or eliminating interference species that can be applied to the membrane system of the preferred embodiments are described in co-pending U.S. patent application Ser. No. 10/896,312 filed Jul. 21, 2004 and entitled "ELECTRODE SYSTEMS FOR ELECTROCHEMICAL SENSORS," Ser. No. 10/991,353, filed Nov. 16, 2004 and entitled, "AFFINITY DOMAIN FOR AN ANALYTE SENSOR," Ser. No. 11/007,635, filed Dec. 7, 2004 and entitled "SYSTEMS AND METHODS FOR IMPROVING ELECTROCHEMICAL ANALYTE SENSORS" and Ser. No. 11/004,561, filed Dec. 3, 2004 and entitled, "CALIBRATION TECHNIQUES FOR A CONTINUOUS ANALYTE SENSOR."

In preferred embodiments, the thickness of the interference domain is from about 0.05 microns or less to about 20 microns or more. In more preferred embodiments, the thickness of the interference domain is between about 0.05, 0.1, 0.15, 0.2, 0.25, 0.3, 0.35, 0.4, 0.45, 0.5, 1, 1.5, 2, 2.5, 3, or 3.5 microns and about 4, 5, 6, 7, 8, 9, 10, 11, 12, 13, 14, 15, 16, 17, 18, 19, or 19.5 microns. In more preferred embodiments, the thickness of the interference domain is from about 0.6, 0.7, 0.8, 0.9, or 1 micron to about 2, 3, or 4 microns.

Electrode Layer

An electrode layer 50 or 147 is situated more proximal to the electrochemically reactive surfaces than the interference layer 48 or 148. To ensure the electrochemical reaction, the electrode layer 50 or 147 includes a semipermeable coating that maintains hydrophilicity at the electrochemically reactive surfaces of the sensor interface. The electrode layer 50 or 147 enhances the stability of the interference layer 48 or 148 by protecting and supporting the material that makes up the interference layer. The electrode layer 50 or 147 also assists in stabilizing the operation of the device by overcoming electrode start-up problems and drifting problems caused by inadequate electrolyte. The buffered electrolyte solution contained in the electrode layer also protects against pH-mediated damage that can result from the formation of a large pH gradient between the substantially hydrophobic interference domain and the electrodes due to the electrochemical activity of the electrodes. In some embodiments, the electrode layer may not be used, for example, when an interference layer is not provided.

In one embodiment, the electrode layer 50 or 147 includes a flexible, water-swellable, substantially solid gel-like film (e.g., a hydrogel) having a "dry film" thickness of from about 0.05 microns to about 100 microns, more preferably from about 0.05, 0.1, 0.15, 0.2, 0.25, 0.3, 0.35, 0.4, 0.45, 0.5, 1, 1.5, 2, 2.5, 3, or 3.5, 4, 4.5, 5, or 5.5 to about 5, 6, 6.5, 7, 7.5, 8, 8.5, 9, 9.5, 10, 10.5, 11, 11.5, 12, 13, 14, 15, 16, 17, 18, 19, 19.5, 20, 30, 40, 50, 60, 70, 80, 90, or 100 microns. In even more preferred embodiments, the thickness of the electrolyte domain is from about 2, 2.5 or 3 microns to about 3.5, 4, 4.5, or 5 microns in the case of a transcutaneously implanted sensor or from about 6, 7, or 8 microns to about 9, 10, 11, or 12 microns in the case of a wholly implanted sensor. "Dry film" thickness refers to the thickness of a cured film cast from a coating formulation onto the surface of the membrane by standard coating techniques.

In some embodiments, the electrode layer 50 or 147 is formed of a curable mixture of a urethane polymer and a hydrophilic polymer. Particularly preferred coatings are formed of a polyurethane polymer having anionic carboxylate functional groups and non-ionic hydrophilic polyether segments, which is crosslinked in the presence of polyvinylpyrrolidone and cured at a moderate temperature of about 50° C. In some preferred embodiments, the electrode layer 50 or 147 is formed from high oxygen soluble materials such as polymers formed from silicone, fluorocarbons, perfluorocarbons, or the like. In one preferred embodiment, the electrode layer 50 or 147 is formed from silicone polymer/hydrophilic polymer blends such as described above.

Underlying the electrode layer is an electrolyte phase is a free-fluid phase including a solution containing at least one compound, typically a soluble chloride salt, which conducts electric current. In one embodiment wherein the membrane system is used with a glucose sensor such as is described herein, the electrolyte phase flows over the electrodes and is in contact with the electrolyte layer. The devices of the preferred embodiments contemplate the use of any suitable electrolyte solution, including standard, commercially available solutions. Generally, the electrolyte phase can have the same osmotic pressure or a lower osmotic pressure than the sample being analyzed. In preferred embodiments, the electrolyte phase comprises normal saline.

In various embodiments, any of the layers discussed above can be omitted, altered, substituted for, and/or incorporated together. For example, a distinct bioprotective layer may not exist. In such embodiments, other domains accomplish the function of the bioprotective layer. As another example, the interference layer can be eliminated in certain embodiments wherein two-electrode differential measurements are employed to eliminate interference, for example, one electrode being sensitive to glucose and electrooxidizable interferants and the other only to interferants, such as is described in U.S. Pat. No. 6,514,718, which is incorporated herein by reference in its entirety. In such embodiments, the interference layer can be omitted.

In one embodiment, the membrane system 18 comprises only two layers. One layer is the enzyme layer as described above. The second layer is positioned more distal than the enzyme layer and serves one or more of the functions described above for the cell disruptive layer, bioprotective layer, and diffusion resistance layer. In one embodiment, this second layer is graduated either structurally and/or chemically as describe above such that different domains of the second layer serve different functions such as cell disruption, bio-protection, or diffusion resistance. In one embodiment, both layers of this membrane system are formed from silicone polymer/hydrophilic polymer blends such as described above.

In one embodiment, every layer in the membrane system 18 is formed from silicone polymer/hydrophilic polymer blends such as described above. Such uniformity in ingredients allows for ease of manufacturing while at the same time allowing for tailoring of properties by varying the ratio of silicone polymer to hydrophilic polymer.

EXAMPLES

Example 1

MED-4840/PLURONIC® F-127 Bioprotective Layer 30 g of PLURONIC® F-127 (PF-127) was dissolved under stirring in 100 g of anhydrous acetone at 40° C. 13 g of acetone was added to 37.3 g of the PF-127 solution followed by adding 4.8 g of dicumyl peroxide (DCP). 40 g of MED-4840 was mixed in a speed mixer at a speed of 3300 rpm for 60 seconds. The MED-4840 mixture was then placed in a motorized mechanical mixer equipped with a spiral dough hook. The mixture was stirred at low speed for 30 s. The stirring speed was then increased to medium-low and the PF-127/DCP solution was added at a rate of 3.5-4.0 g every 30 seconds. After all of the PF-127/DCP solution was added, the mixture was stirred at medium speed for 3 minutes. The mixture was then placed in a Speed Mixer and mixed at 3300 rpm for 60 seconds. This process was repeated until the desired viscosity was reached.

5-10 mL of the mixture was placed in an evenly-distributed line between the arms of the drawdown blade on a drawdown machine. The drawdown machine was used to create a 9 inch long and 0.0045 inch thick film at a speed of about 0.7 inches/minute. A preformed piece of porous silicone (to act as a cell disruptive layer) was placed skin side down on the drawn film and tapped lightly to promote the polymeric mixture to penetrate into the pores of the porous silicone. The film was then cured for 1.5 hours at 100° C.

Example 2

MED-4840/PLURONIC® F-127 Diffusion Resistance Layer on Implanted Sensor

A MED-4840/PLURONIC® F-127 membrane was manufactured using 8.4% PLURONIC® and 1.8% of a DCP cross-linking agent. This membrane was placed over a two-layer membrane having an enzyme layer and an electrode layer. The combined membrane layers were placed on a wholly implantable glucose sensor. The sensor was sterilized and implanted into a diabetic rat model. FIG. 6 is a graph depicting the resulting glucose sensor measurements over the course of approximately two months. The small points in FIG. 6 depict glucose concentrations measured by the sensor and the large points depict glucose concentrations measured by separate blood glucose assays. The graph indicates a close correlation between the sensor glucose measurements and the blood glucose measurements.

Example 3

MED-4840/PLURONIC® F-127 Bioprotective Layer on Implanted Sensor

Figure 7:
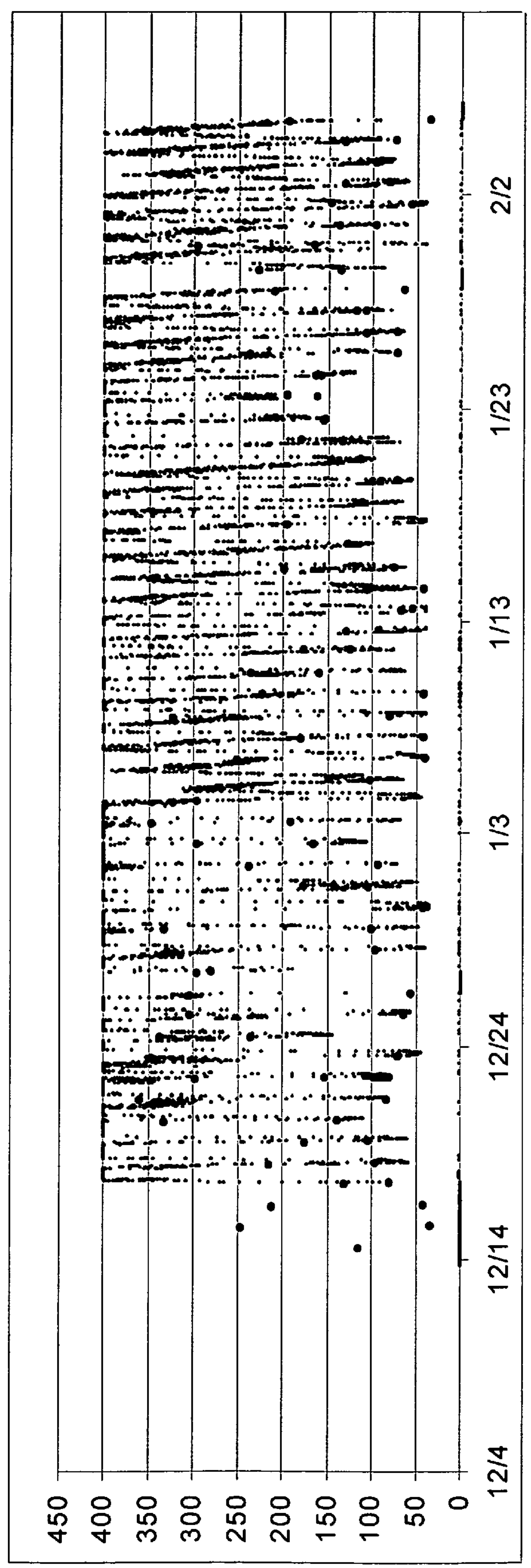
FIG. 7 is a graph depicting glucose measurements from a sensor including a silicon/hydrophilic-hydrophobic polymer blend in a bioprotective layer implanted in a diabetic rat model.

A MED-4840/PLURONIC® F-127 membrane was manufactured using 20% PLURONIC® and a 20:1 ratio of DCP cross-linking agent per PLURONIC®. Prior to curing, the material was drawn down and a cell-disruptive porous silicone membrane was placed on the uncured layer. After curing, the combined bioprotective/porous silicone membrane was placed over a four-layer membrane having a diffusion resistance layer, enzyme layer, interference layer, and electrode layer. The combined membrane layers were placed on a wholly implantable glucose sensor. The sensor was sterilized and implanted into a diabetic rat model. FIG. 7 is a graph depicting the resulting glucose sensor measurements over the course of approximately two months. The small points in FIG. 7 depict glucose concentrations measured by the sensor and the large points depict glucose concentrations measured by separate blood glucose assays. The graph indicates a close correlation between the sensor glucose measurements and the blood glucose measurements.

Example 4

MED-4840/PLURONIC® F-127 Diffusion Resistance Layer Interference Properties

Figure 8:
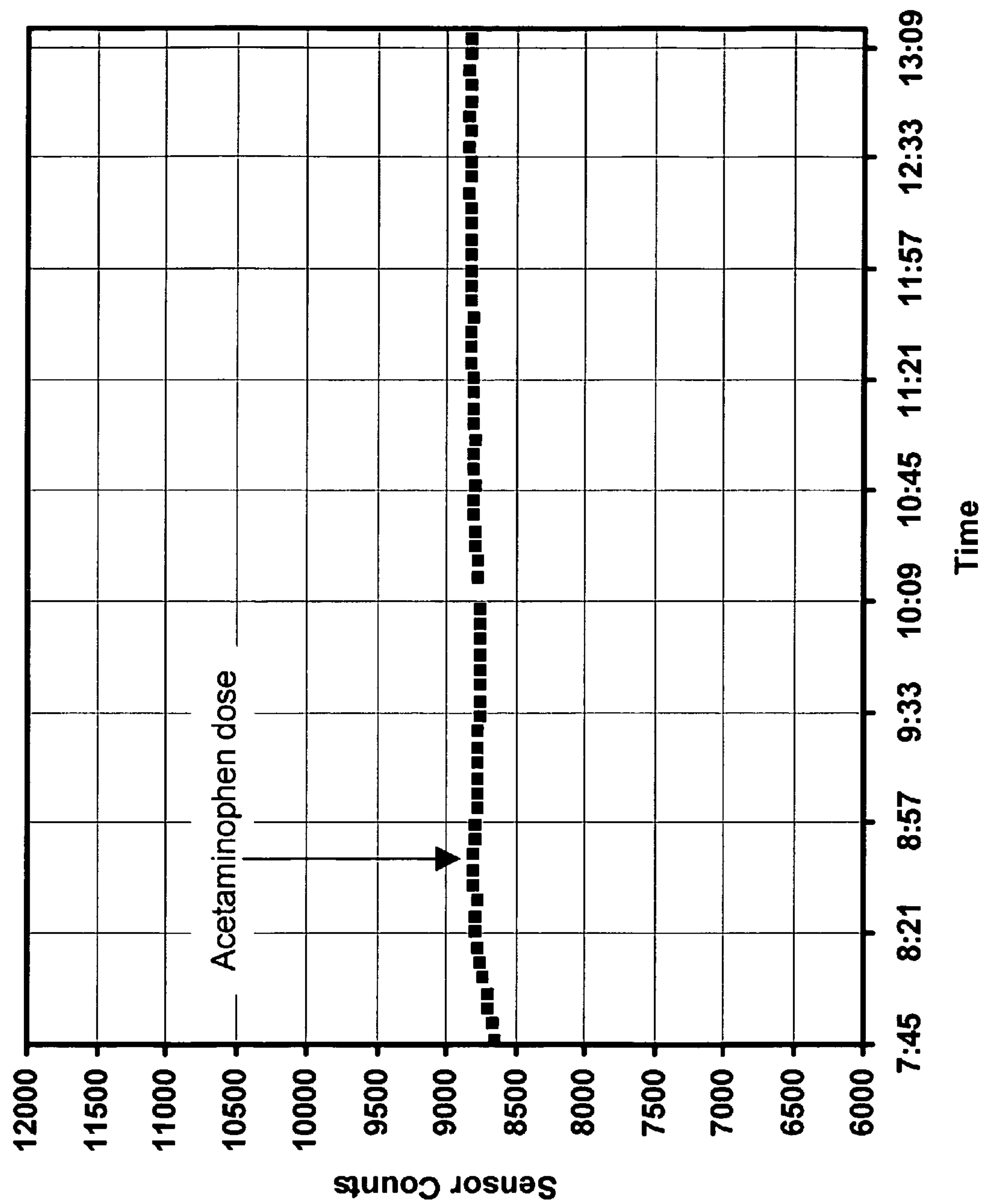
FIG. 8 is a graph depicting a sensor signal from a sensor including a silicon/hydrophilic-hydrophobic polymer blend membrane exposed to acetaminophen.

A MED-4840/PLURONIC® F-127 membrane was manufactured using 8.4% PLURONIC® and 3.7% DCP. This membrane was placed over two-layer membrane having an electrode layer and an enzyme layer. The combined membrane layers were installed on a wholly implantable glucose sensor. The sensor was placed into a 2 L bath filled with PBS (saline). The continuously stirred bath was brought to 37° C. and the sensor allowed to equilibrate for a minimum of 1 hour until the sensors reached a flat line continuous baseline signal. Acetaminophen was then added to the bath to a dilution of 3.8 mg/dl. The sensor was then allowed to equilibrate over 1 hour while measurements were continuously recorded from the sensor. FIG. 8 is a graph show the sensor signal over the course of the hour. The graph indicates that the signal changed by less than 1%. Thus, the sensor was substantially insensitive to the presence of acetaminophen, indicating that the membrane substantially reduces transport of acetaminophen therethrough.

Figure 9:
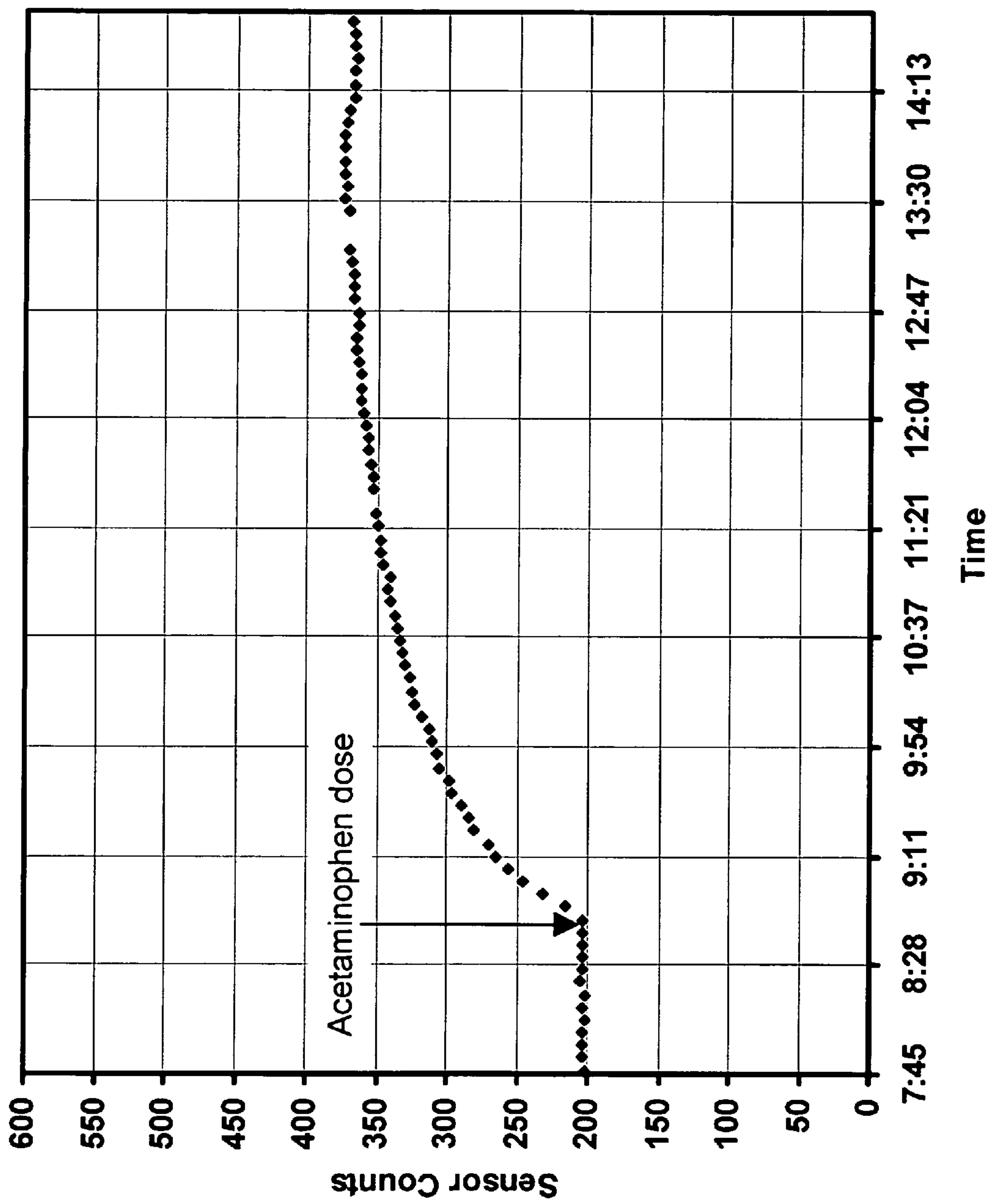
FIG. 9 is a graph depicting a sensor signal from a sensor not including a silicon/hydrophilic-hydrophobic polymer blend membrane exposed to acetaminophen.

As a comparative example, a wholly implantable glucose sensor with a membrane not including a silicone/hydrophilic-hydrophobic polymer blend was tested. The membrane in this sensor included a three-layer membrane having an electrode layer, an enzyme layer, and a polyurethane diffusion resistance layer. A porous silicone cell disruptive layer was added on top. The sensor was placed into a 2 L bath filled with PBS (saline). The continuously stirred bath was brought to 37° C. and the sensor allowed to equilibrate for a minimum of 1 hour until the sensors reached a flat line continuous baseline signal. Acetaminophen was then added to the bath to a dilution of 3.8 mg/dl. The sensor was then allowed to equilibrate over 1 hour while measurements were continuously recorded from the sensor. FIG. 9 is a graph show the sensor signal over the course of the hour. The graph indicates that the signal changed by more than 15% after introduction of the acetaminophen. Thus, without the silicone/hydrophilic-hydrophobic polymer blend sensor was sensitive to the acetaminophen interferant.

Methods and devices that are suitable for use in conjunction with aspects of the preferred embodiments are disclosed in U.S. Pat. Nos. 4,994,167; 4,757,022; 6,001,067; 6,741,877; 6,702,857; 6,558,321; 6,931,327; and 6,862,465.

Methods and devices that are suitable for use in conjunction with aspects of the preferred embodiments are disclosed in U.S. Publication No. US-2005-0176136-A1; U.S. Publication No. US-2005-0251083-A1; U.S. Publication No. US-2005-0143635-A1; U.S. Publication No. US-2005-0181012-A1; U.S. Publication No. US-2005-0177036-A1; U.S. Publication No. US-2005-0124873-A1; U.S. Publication No. US-2005-0051440-A1; U.S. Publication No. US-2005-0115832-A1; U.S. Publication No. US-2005-0245799-A1; U.S. Publication No. US-2005-0245795-A1; U.S. Publication No. US-2005-0242479-A1; U.S. Publication No. US-2005-0182451-A1; U.S. Publication No. US-2005-0056552-A1; U.S. Publication No. US-2005-

0192557-A1; U.S. Publication No. US-2005-0154271-A1; U.S. Publication No. US-2004-0199059-A1; U.S. Publication No. US-2005-0054909-A1; U.S. Publication No. US-2005-0112169-A1; U.S. Publication No. US-2005-0051427-A1; U.S. Publication No. US-2003-0032874; U.S. Publication No. US-2005-0103625-A1; U.S. Publication No. US-2005-0203360-A1; U.S. Publication No. US-2005-0090607-A1; U.S. Publication No. US-2005-0187720-A1; U.S. Publication No. US-2005-0161346-A1; U.S. Publication No. US-2006-0015020-A1; U.S. Publication No. US-2005-0043598-A1; U.S. Publication No. US-2003-0217966-A1; U.S. Publication No. US-2005-0033132-A1; U.S. Publication No. US-2005-0031689-A1; U.S. Publication No. US-2004-0045879-A1; U.S. Publication No. US-2004-0186362-A1; U.S. Publication No. US-2005-0027463-A1; U.S. Publication No. US-2005-0027181-A1; U.S. Publication No. US-2005-0027180-A1; U.S. Publication No. US-2006-0020187-A1; U.S. Publication No. US-2006-0036142-A1; U.S. Publication No. US-2006-0020192-A1; U.S. Publication No. US-2006-0036143-A1; U.S. Publication No. US-2006-0036140-A1; U.S. Publication No. US-2006-0019327-A1; U.S. Publication No. US-2006-0020186-A1; U.S. Publication No. US-2006-0020189-A1; U.S. Publication No. US-2006-0036139-A1; U.S. Publication No. US-2006-0020191-A1; U.S. Publication No. US-2006-0020188-A1; U.S. Publication No. US-2006-0036141-A1; U.S. Publication No. US-2006-0020190-A1; U.S. Publication No. US-2006-0036145-A1; U.S. Publication No. US-2006-0036144-A1; and U.S. Publication No. US-2006-0016700A1.

Methods and devices that are suitable for use in conjunction with aspects of the preferred embodiments are disclosed in U.S. Application Ser. No. 09/447,227 filed Nov. 22, 1999 and entitled "DEVICE AND METHOD FOR DETERMINING ANALYTE LEVELS"; U.S. Application Ser. No. 11/280,672 filed Nov. 16, 2005, and entitled "TECHNIQUES TO IMPROVE POLYURETHANE MEMBRANES FOR IMPLANTABLE GLUCOSE SENSORS"; U.S. Application Ser. No. 11/280,102 filed Nov. 16, 2005, and entitled "TECHNIQUES TO IMPROVE POLYURETHANE MEMBRANES FOR IMPLANTABLE GLUCOSE SENSORS"; U.S. Application Ser. No. 11/201445 filed Aug. 10, 2005 and entitled "SYSTEM AND METHODS FOR PROCESSING ANALYTE SENSOR DATA"; U.S. Application Ser. No. 11/335879 filed Jan. 18, 2006 and entitled "CELLULOSIC-BASED INTERFERENCE DOMAIN FOR AN ANALYTE SENSOR"; U.S. Application Ser. No. 11/334876 filed Jan. 18, 2006 and entitled "TRANSCUTANEOUS ANALYTE SENSOR"; U.S. Application Ser. No. 11/333837 filed Jan. 17, 2006 and entitled "LOW OXYGEN IN VIVO ANALYTE SENSOR".

All references cited herein are incorporated herein by reference in their entireties. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A device for use in an implantable analyte sensor, comprising:
- an enzyme layer comprising an enzyme; and
- a diffusion resistance layer comprising a silicone elastomer and a poly(ethylene oxide) and poly(propylene oxide) co-polymer, wherein the diffusion resistance layer is positioned between the enzyme layer and tissue adjacent to the sensor when implanted.

2. The device of claim 1, further comprising a bioprotective layer positioned between the diffusion resistance layer and tissue adjacent to the sensor when implanted.

3. The device of claim 1, wherein the silicone elastomer is a dimethyl-siloxane and methyihydrogen-siloxane copolymer.

4. The device layer of claim 3, wherein the silicone elastomer comprises vinyl substituents.

5. The device of claim 1, wherein the silicone elastomer is an elastomer produced by curing a MED-4840 mixture.

6. The device of claim 1, wherein the copolymer comprises hydroxy substituents.

7. The device of claim 1, wherein the co-polymer is a PLURONIC® polymer.

8. The device of claim 1, wherein the co-polymer is PLURONIC® F-127.

9. The device of claim 1, wherein the analyte is glucose.

10. The device of claim 1, wherein at least a portion of the co-polymer is cross-linked.

11. The sensor device of claim 1, wherein from about 5% w/w to about 30% w/w of the diffusion resistance layer is the co-polymer.

12. The device of claim 1, wherein the ratio of the silicone elastomer to co-polymer varies within the diffusion resistance layer.

13. The device of claim 1, wherein the sensor is configured to be wholly implanted.

14. The device of claim 1, wherein the sensor is configured to be transcutaneously implanted.

15. A device for use in an implantable analyte sensor, comprising at least one polymer membrane comprising an enzyme, wherein every polymer membrane in said sensor comprises a silicone elastomer and a poly(ethylene oxide) and poly(propylene oxide) co-polymer.

16. The device of claim 15, wherein the silicone elastomer is a dimethyl-siloxane and methylhydrogen-siloxane copolymer.

17. The device of claim 16, wherein the silicone elastomer comprises vinyl substituents.

18. The device of claim 15, wherein the silicone elastomer is an elastomer produced by curing a MED-4840 mixture.

19. The device of claim 15, wherein the copolymer comprises hydroxy substituents.

20. The device of claim 15, wherein the co-polymer is a PLURONIC® polymer.

21. The device of claim 15, wherein the co-polymer is PLURONIC® F-127.

22. The device of claim 15, wherein at least a portion of the co-polymer is cross-linked.

23. The device of claim 15, wherein from about 5% w/w to about 30% w/w of each polymer membrane is the co-polymer.

24. The device of claim 15, wherein the sensor comprises at least two polymer membranes having a ratio of the silicone elastomer to the co-polymer that is different.

25. The device of claim 15, wherein the sensor is configured to be wholly implanted.

26. The device of claim 15, wherein the sensor is configured to be transcutaneously implanted.

27. An analyte sensor, comprising:

a working electrode; and a membrane disposed over the working electrode, the membrane comprising:

an enzyme layer comprising an enzyme, and an additional layer disposed over the enzyme layer comprising a silicone elastomer and a poly(ethylene oxide) and poly(propylene oxide) co-polymer.

28. The sensor of claim 27, wherein the analyte is glucose.

29. The sensor of claim 27, wherein the enzyme is glucose oxidase.

30. The sensor of claim 27, wherein the additional layer is adapted to resist diffusion of the analyte therethrough.

31. The sensor of claim 27, wherein the additional layer is adapted to resist cellular attachment.

32. The sensor of claim 27, wherein the additional layer is impermeable to cells.

33. The sensor of claim 27, wherein the additional layer is resistant to the effects of one or more oxidative species.

34. The sensor of claim 27, wherein at least a portion of the additional layer is porous.

35. The sensor of claim 27, wherein the ratio of the silicone elastomer to co-polymer varies within the additional layer.

36. The sensor of claim 27, wherein the porosity of the additional layer varies from one side of the layer to the other.

37. The sensor of claim 27, wherein the silicone elastomer is a dimethyl-siloxane and methylhydrogen-siloxane copolymer.

38. The sensor of claim 27, wherein the silicone elastomer comprises vinyl substituents.

39. The sensor of claim 27, wherein the silicone elastomer is an elastomer produced by curing a MED-4840 mixture.

40. The sensor of claim 27, wherein the copolymer comprises hydroxy substituents.

41. The sensor of claim 27, wherein the co-polymer is a PLURONIC® polymer.

42. The sensor of claim 27, wherein the co-polymer is PLURONIC® F-127.

43. The sensor of claim 27, wherein at least a portion of the co-polymer is cross-linked.

44. The sensor of claim 27, wherein from about 5% w/w to about 30% w/w of the additional layer is the co-polymer.

45. An analyte sensor, comprising:

a working electrode;

an enzyme layer disposed over the working electrode and comprising an enzyme; and an additional layer, wherein the additional layer comprises a blend of a silicone polymer and a hydrophilic polymer, wherein the additional layer is adapted to substantially prevent penetration of one or more interferants into an electrolyte phase adjacent to the working electrode.

46. The sensor of claim 45, wherein the one or more interferants comprise acetaminophen.

47. The sensor of claim 45, wherein the additional layer is positioned between the working electrode and the enzyme layer.

48. The sensor of claim 45, wherein the additional layer is disposed over the enzyme layer.

49. The sensor of claim 45, wherein the analyte is glucose.

50. The sensor of claim 45, wherein the enzyme is glucose oxidase.

51. The sensor of claim 45, wherein the silicone polymer is a dimethyl-siloxane and methylhydrogen-siloxane copolymer.

52. The sensor of claim 45, wherein the silicone polymer comprises vinyl substituents.

53. The sensor of claim 45, wherein the silicone polymer is an elastomer produced by curing a MED-4840 mixture.

54. The sensor of claim 45, wherein the hydrophilic polymer is a poly(ethylene oxide) and poly(propylene oxide) copolymer.

55. The sensor of claim 54, wherein the copolymer comprises hydroxy substituents.

56. The sensor of claim 54, wherein the co-polymer is a PLURONIC® polymer.

57. The sensor of claim 54, wherein the co-polymer is PLURONIC® F-127.

58. The sensor of claim 54, wherein at least a portion of the co-polymer is cross-linked.

59. The sensor of claim 45, wherein from about 5% w/w to about 30% w/w of the additional layer is the hydrophilic polymer.

* * * * *

UNITED STATES PATENT AND TRADEMARK OFFICE

CERTIFICATE OF CORRECTION

PATENT NO. : 7,613,491 B2
APPLICATION NO. : 11/404417
DATED : November 3, 2009
INVENTOR(S) : Boock et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 677 days.

Signed and Sealed this

Nineteenth Day of October, 2010

David J. Kappos

*Director of the United States Patent and Trademark Office*

UNITED STATES PATENT AND TRADEMARK OFFICE

CERTIFICATE OF CORRECTION

PATENT NO. : 7,613,491 B2
APPLICATION NO. : 11/404417
DATED : November 3, 2009
INVENTOR(S) : Boock et al.

It is certified that error appears in the above-identified patent and that said Letters Patent is hereby corrected as shown below:

| Issued Patent Column | Line | Description of Discrepancy |
|---|---|---|
| (Item 56) Page 7 Col. 1 | 6 | Under Other Publications, change "www. Answers.com" to --www.Answers.com--. |
| (Item 56) Page 7 Col. 1 | 26 | Under Other Publications, change "Senso" to --Sensor--. |
| (Item 56) Page 7 Col. 2 | 16 | Under Other Publications, change "impintable," to --implantable,--. |
| (Item 56) Page 7 Col. 2 | 21 | Under Other Publications, change "Enzymlology," to --Enzymology,--. |
| (Item 56) Page 8 Col. 1 | 58 | Under Other Publications, change "ultrasmall" to --ultra-small--. |
| (Item 56) Page 8 Col. 1 | 64 | Under Other Publications, change "Aniodic" to --Anodic--. |
| (Item 56) Page 9 Col. 1 | 19 | Under Other Publications, change "Electronanalysis" to --Electroanalysis--. |
| (Item 56) Page 9 Col. 1 | 42 | Under Other Publications, change "amperometeric" to --amperometric--. |
| (Item 56) Page 9 Col. 2 | 16 | Under Other Publications, change "Apllied" to --Applied--. |

Signed and Sealed this
Twenty-second Day of November, 2011

David J. Kappos
*Director of the United States Patent and Trademark Office*

| | | |
|---|---|---|
| (Item 56) Page 9 Col. 2 | 52 | Under Other Publications, change “Bromedical” to --Biomedical--. |
| (Item 56) Page 10 Col. 1 | 32 | Under Other Publications, change “Subcutaenous” to --Subcutaneous--. |
| (Item 56) Page 10 Col. 1 | 46 | Under Other Publications, change “Membran,” to --Membrane,--. |
| (Item 56) Page 10 Col. 1 | 50 | Under Other Publications, change “25(10)1840” to --25(10):1840--. |
| (Item 56) Page 10 Col. 2 | 6 | Under Other Publications, change “pancrease” to --pancreas--. |
| (Item 56) Page 10 Col. 2 | 47 | Under Other Publications, change “Membrance” to --Membrane--. |
| (Item 56) Page 11 Col. 1 | 18 | Under Other Publications, change “impleated” to --implanted--. |
| (Item 56) Page 11 Col. 1 | 25 | Under Other Publications, change “Tranducers” to --Transducers--. |
| (Item 56) Page 11 Col. 2 | 1 | Under Other Publications, change “in” to --In--. |
| 4 | 64 | Change “andrenostenedione” to --androstenedione--. |
| 5 | 12 | Change “diptheria” to --diphtheria--. |
| 5 | 19 | Change “perioxidase;” to --peroxidase:--. |
| 5 | 28 | Change “sissomicin;” to --sisomicin;--. |
| 5 | 31 | Change “Echinococus” to --Echinococcus--. |
| 5 | 32 | Change “Entamobea” to --Entamoeba--. |
| 5 | 32-33 | Change “Giardia duodenalisa” to --Giardia duodenalis--. |
| 5 | 40 | Change “Trepenoma pallidium,” to --Treponema pallidum,--. |
| 5 | 41 | Change “stomatis” to --stomatitis--. |

| 5 | 62 | Change “barbituates”<br>to --barbiturates--. |
|---|---|---|
| 6 | 40 | Change “(2H$_+$),”<br>to --(2H$^+$),--. |
| 10 | 32 | Change “(2H+),”<br>to --(2H$^+$),--. |
| 10 | 32 | Change “(2e-),”<br>to --(2e$^-$),--. |
| 17 | 28 | Change “SYNPERONICS”<br>to --SYNTRONICS--. |
| 19 | 33 | Change “phospazenes,”<br>to --phosphazenes,--. |
| 19 | 37 | Change “hydyoxyethyl”<br>to --hydroxyethyl--. |
| 20 | 41 | Change “phospazenes,”<br>to --phosphazenes,--. |
| 20 | 45 | Change “hydyoxyethyl”<br>to --hydroxyethyl--. |
| 22 | 16 | Change “phospazenes,”<br>to --phosphazenes,--. |
| 22 | 20 | Change “hydyoxyethyl”<br>to --hydroxyethyl--. |
| 23 | 11 | Change “oxid”<br>to --oxide--. |
| 26 | 33 | Change “Nafion®”<br>to --Nafion®,--. |
| 31 | 30 | Change “0016700A1.”<br>to --0016700-A1.--. |
| 32 | 31 | In Claim 3, change “methyihydrogen”<br>to --methylhydrogen--. |
| 32 | 46 | In Claim 11, change “The sensor device”<br>to --The device--. |